United States Patent
D'Alessio et al.

(10) Patent No.: US 8,323,262 B2
(45) Date of Patent: Dec. 4, 2012

(54) SELF-CONTAINED MEDICAL APPLICATORS FOR MULTIPLE COMPONENT FORMULATIONS, AND METHODS OF USE THEREOF

(75) Inventors: Keith R. D'Alessio, Cary, NC (US);
Jeffrey G. Clark, Raleigh, NC (US);
Roy R. B. Attride, Raleigh, NC (US);
Wai N. Chin, Glenview, IL (US);
Robert M. Colonna, Newton, MA (US);
Tomas Matusaitis, Chicago, IL (US);
Todd J. Taylor, Cambridge, MA (US);
Christopher R. Yahnker, Raleigh, NC (US)

(73) Assignee: HyperBranch Medical Technology, Inc., Durham, NC (US)

( * ) Notice: Subject to any disclaimer, the term of this patent is extended or adjusted under 35 U.S.C. 154(b) by 818 days.

(21) Appl. No.: 12/499,469

(22) Filed: Jul. 8, 2009

(65) Prior Publication Data
US 2010/0010473 A1 Jan. 14, 2010

Related U.S. Application Data

(60) Provisional application No. 61/078,893, filed on Jul. 8, 2008.

(51) Int. Cl.
*A61M 37/00* (2006.01)
(52) U.S. Cl. .......................................... 604/520; 604/87
(58) Field of Classification Search .............. 604/82–91, 604/520, 416, 191; 606/213
See application file for complete search history.

(56) References Cited

U.S. PATENT DOCUMENTS

| | | | | |
|---|---|---|---|---|
| 3,678,931 | A * | 7/1972 | Cohen | 604/90 |
| 4,055,177 | A * | 10/1977 | Cohen | 604/88 |
| 4,886,495 | A * | 12/1989 | Reynolds | 604/88 |
| 5,116,315 | A * | 5/1992 | Capozzi et al. | 604/82 |
| 5,314,412 | A * | 5/1994 | Rex | 604/191 |
| 5,364,369 | A * | 11/1994 | Reynolds | 604/187 |
| 5,605,255 | A * | 2/1997 | Reidel et al. | 222/137 |
| 5,759,171 | A * | 6/1998 | Coelho et al. | 604/82 |
| 6,079,868 | A * | 6/2000 | Rydell | 366/189 |
| 6,648,852 | B2 * | 11/2003 | Wirt et al. | 604/86 |
| 6,902,543 | B1 * | 6/2005 | Cherif-Cheikh et al. | 604/82 |
| 2002/0099343 | A1 | 7/2002 | Garcia | |
| 2007/0213660 | A1 * | 9/2007 | Richards et al. | 604/82 |
| 2008/0103564 | A1 * | 5/2008 | Burkinshaw et al. | 607/96 |

FOREIGN PATENT DOCUMENTS

WO WO-99/44672 A1 9/1999

OTHER PUBLICATIONS

International Search Report dated Mar. 2, 2010.

* cited by examiner

*Primary Examiner* — Kevin C Sirmons
*Assistant Examiner* — Michael J Anderson
(74) *Attorney, Agent, or Firm* — Dana M. Gordon; Foley Hoag LLP

(57) ABSTRACT

Certain aspects of the invention relate to an applicator, and methods of use thereof, which can house multiple component formulations in separate material receptacles, which can then be easily reconstituted at time of use without any assembly by the user. A device of the invention can be used for, but is not limited to, applying hydrogel formulations to dura mater, abdominal tissue in hernia repair, tissues near the spine, lung tissue, intestinal tissue, and any of the internal tissues. A device of the invention can be configured to apply a spray or a stream of liquid formulation onto a surface to be treated. A device of the invention can be configured to deliver the formulation through an endoscope or laparoscope.

20 Claims, 11 Drawing Sheets

[A]

[B]

Figure 1:
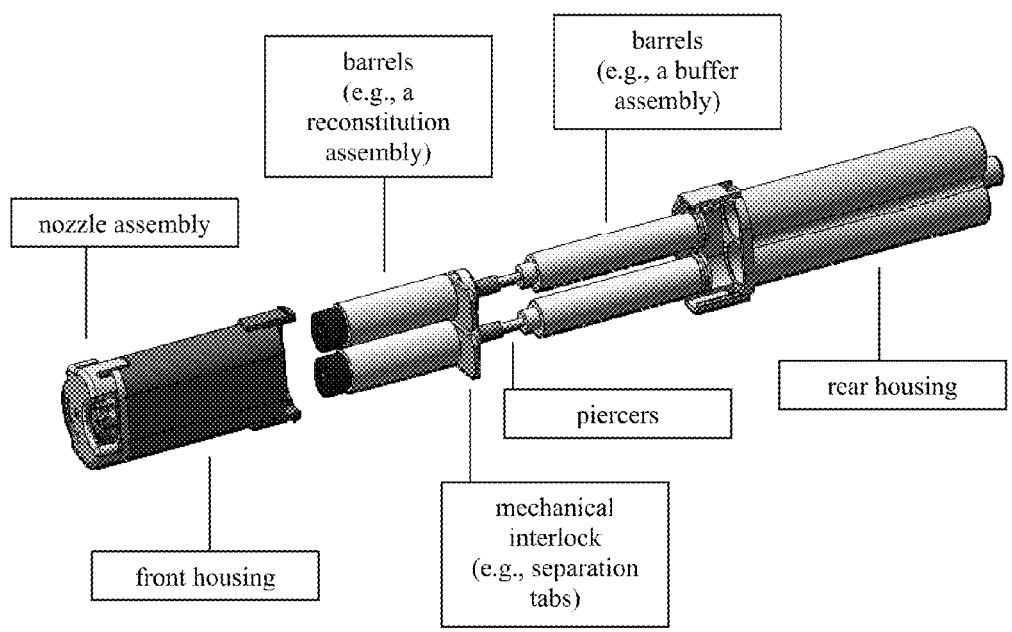

SELF-CONTAINED MEDICAL APPLICATORS FOR MULTIPLE COMPONENT FORMULATIONS, AND METHODS OF USE THEREOF

RELATED APPLICATION

This application claims the benefit of priority to U.S. Provisional Patent Application Ser. No. 61/078,893, filed Jul. 8, 2008; which is hereby incorporated by reference in its entirety.

BACKGROUND

A number of medically useful compositions comprise two or more ingredients that are not mixed together until shortly prior to use. In some instances, at least one of the ingredients is a solid, often a powder, while at least one of the other ingredients is a liquid in which the solid ingredient is to be dissolved. Therefore, it is desired to have an applicator that can easily deliver formulations for use in the body which incorporates multiple components which need to be separated during storage and mixed just prior to application.

Use of a dual-ingredient composition can be accomplished with a conventional syringe by first loading one ingredient into the syringe, then adding the second ingredient, shaking the syringe or otherwise agitating the contents to achieve mixing, and subsequently dispensing the resulting mixture in the usual manner. This procedure, however, presents substantial shortcomings, including contamination and loss of sterility. For example, using a conventional syringe of the kind that is filled through a fill needle connected to the outlet orifice of the syringe, it is necessary to replace the needle after the first ingredient has been drawn into the syringe in order to avoid contamination of the supply of the second ingredient. Even then it may be difficult to complete the procedure without rendering the outlet portion of the syringe non-sterile, particularly by extended contact with air.

Another technique that may be employed utilizes a syringe of generally conventional construction in which one ingredient has initially been loaded into the syringe, usually followed by a sterilization procedure. Again, however, it is often rather difficult to load the syringe with the second ingredient without affecting the sterile characteristics of the syringe. Moreover, in both of these procedures the user's manipulative steps are complex enough that some difficulty may be experienced.

Medical sealants and adhesives play an important role in helping patients recover from surgery or trauma. Further, such compositions may comprise two or more ingredients that are not mixed together until shortly prior to use. In particular, sealants and adhesives are useful in treating patients suffering from a variety of internal or topical conditions, including lacerations, tears, wounds, ulcers, anastomoses, and surgical procedures. Sealants or adhesives can generally be used in any indication or application for which a suture or staple is presently used, and the sealant or adhesive often provides a better outcome than a suture or staple. Sealants or adhesives can also be applied more quickly to the injury site and often provide a better seal over the wound, and ultimately improved healing, in comparison to a conventional suture or staple.

There are two medical sealant/adhesive products, CoSeal and DuraSeal, currently on the market which are based on hydrogel formulations. Both products comprise multiple components housed in separate containers. CoSeal Surgical Sealant (CoSeal) is composed of two synthetic polyethylene glycols (PEGs), a dilute hydrogen chloride solution and a sodium phosphate/sodium carbonate solution. The DuraSeal Dural Sealant System consists of components for preparation of a synthetic, absorbable sealant and an applicator for delivery of the sealant to the target site the sealant is composed of two solutions, a polyethylene glycol (PEG) ester solution and a trilysine amine solution. However, the products have shortcomings because the devices need to be assembled at the time of use and they utilize static mixing systems that allow the hydrogel formulation to gel within the mixing nozzle, precluding a start-and-stop application technique.

Fibrin glues are also sold in packaging and applicator systems that are similar to those used for CoSeal and DuraSeal. One example is Baxter's Tisseel. Tisseel VH [Fibrin Sealant] consists of a two-component fibrin biomatrix that offers highly concentrated human fibrinogen to seal tissue and stop diffuse bleeding.

Baxter also offers different types of applicators, for example, Duploject; Easyspray; and DuploSpray MIS. Duploject is a reconstitution device that offers needle free easy preparation. Easyspray is a disposable set consisting of a dual-lumen connector hose, a sterile filter, two spray heads and a clip to be attached to the Duploject plunger for gas activation. DuploSpray MIS applicator is a disposable spray applicator consisting of a stainless steel shaft, dual lumen spray tubing, sterile filter and two replaceable spray tips.

Further, Micromedics, Inc. a medical device manufacturer in St. Paul, Minn., manufactures an endoscopic spray system for biomaterials called the FibriJet. FibriJet incorporates a gas-assisted spray system. Spraying of fibrin glues are also discussed in the patent literature; see: U.S. Pat. Nos. 5,474,540; 4,874,368; and 5,368,563; all of which are hereby incorporated by reference.

SUMMARY

Certain aspects of the invention relate to an applicator, and methods of use thereof, which can house multiple component formulations in separate material receptacles, which can then be easily reconstituted at time of use with little or no assembly by the user. A further objective of the invention is to provide an applicator system for which the manipulative steps required for use are held to a minimum and/or the number of device components is held to a minimum.

In certain embodiments, a device of the invention can be used for, but is not limited to, applying hydrogel formulations to dura mater, abdominal tissue in hernia repair, tissues near the spine, lung tissue, intestinal tissue, and any of the internal tissues. In certain embodiments, a device of the invention can be configured to apply a spray or a stream of liquid formulation onto a surface to be treated. In certain embodiments, a device of the invention can be configured to deliver the formulation through a trocar in a scope (e.g., an endoscope or laparoscope).

One aspect of the invention relates to an applicator system, and methods of use thereof, that can be used to house separately two liquids and two solids (e.g., components of a polymerizable hydrogel), is further designed to facilitate the reconstitution of the solids inside the applicator, and is also designed to facilitate the application of the mixture to a surface. In certain embodiments, such an applicator may be used for delivering a composition to a tissue. For example, such an applicator may be used for delivering a formulation to the dura or a cornea. In addition, the applicators may be useful for a variety of other applications, including, for example, preparation and application of a vascular sealant or arterial access closures.

In certain embodiments, the applicator contains at least two sealed chambers: a first chamber containing a solid; and a second chamber containing a liquid. When a user wishes to use the applicator, he or she causes the an element of the liquid-containing chamber to pierce the solid-containing chamber, and a plunger within the liquid-containing chamber to force the liquid into the solid-containing chamber. In certain embodiments the liquid passes through a check valve. The liquid flows through a passage located in a piston located in the solid-containing chamber, and the liquid then comes into contact with the solid. Continued advancement of the plunger causes the piercer to come to rest within the piston, thereby sealing the passage through the piston. The applicator can then be optionally agitated to promote thorough mixing of the solid and the liquid. Continued motion of the plunger, and thereby the piston, expels the solid/liquid mixture into a nozzle assembly, and then onto or into a patient. In certain embodiments, compressed gas is used to effectuate the piercing of the solid-containing chamber and the movement of the plunger.

In certain embodiments, the present invention describes how the functionality of a spray applicator can be extended beyond what is normally possible for a spray applicator system. In certain embodiments, a precision orifice is placed within the nozzle assembly so as to control the flow of material out of the nozzle. In certain embodiments, a tubular fitment is added to the very distal end of the air assisted spray applicator to limit the width of spray application. In certain embodiments, the fitments allows for a surgeon to apply a hydrogel formulation across a gap of loosely approximately tissue surfaces. In certain embodiments, the fitment consists of a spatula-like piece which is placed under the incision line and allows for the formulation to be sprayed over a gap and yet still form a integrated leak-free application of formulation to loosely approximated tissues such as dura mater.

BRIEF DESCRIPTION OF THE FIGURES

FIG. 1 depicts an exploded view of a pen-like embodiment of a device of the invention, comprising a nozzle assembly, a first housing which houses a reconstitution assembly, separation tabs, and a rear housing which houses a buffer solution assembly.

FIG. 2 depicts a pen-like embodiment of a device of the invention, showing a top and side view.

FIG. 3 depicts a gun-like embodiment of a device of the invention, showing a top and side view, highlighting a window in the top view which allows a user to see the amount of undispensed material left in the device.

FIG. 4 depicts a spring-loaded pen-like embodiment of a device of the invention, showing a top and side view.

FIG. 5 depicts a pressurized pen-like embodiment of a device of the invention, showing a top and side view.

FIG. 6 depicts an electronic pen-like embodiment of a device of the invention, highlighting a use of the device.

FIG. 7 depicts a gun-like embodiment of a device of the invention, highlighting different aspects of the design and a use of the embodiment.

FIG. 8 depicts a cut-away view of a gun-like embodiment of a device of the invention.

FIG. 9 depicts [A] a fitment with a flattened end; and [B] a fitment with a spatula-like piece.

FIG. 10 depicts one embodiment with precision orifices in the fluid delivery path of the nozzle.

FIG. 11 depicts one embodiment with check valves in the liquid flow path, to avoid backflow of material from a proximal to a distal chamber.

DETAILED DESCRIPTION

There is a need to develop improved medical dispensers that facilitate the complete mixing of solids and/or liquids inside the dispenser while maintaining the sterility of the mixture. In addition, there is need for medical dispensers that allow two or more components which are to be mixed to be kept separate until just prior to use. Further, it would be advantageous if the dispensers could also act as applicators, thereby facilitating the application of the mixture. The present invention addresses these needs and others.

One aspect of the invention relates to an applicator system that may be used to house multiple components (e.g., components of a polymerizable hydrogel, such as solids and liquids), facilitating the mixing of the components inside the applicator, and further facilitating the application of the mixture. Another aspect of the invention relates to an applicator system that may be used to house multiple liquids and a solid (e.g., components of a polymerizable hydrogel), facilitating the mixing of the solid and liquids inside the applicator, and further facilitating the application of the mixture. Another aspect of the invention relates to an applicator system that may be used to house two liquids and two solids (e.g., components of a polymerizable hydrogel), facilitating the mixing of the solid and liquid inside the applicator, and further facilitating the application of the mixture. Another aspect of the invention relates to an applicator system that may be used to house two liquids and one solids (e.g., components of a polymerizable hydrogel), facilitating the mixing of the solid and liquid inside the applicator, and further facilitating the application of the mixture.

While the invention will often be described herein as facilitating the formation and effective delivery of a polymerizable hydrogel formulation to a patient, this characterization is not intended in any way to limit the scope of the invention to such an application. Rather, the applicators of the invention, and the methods of the invention, may be used in any application requiring mixing two or more components (e.g., solids and liquids) prior to use. It is understood that these applicators may be useful for a variety of applications including, for example, preparation and application of a vascular sealant and arterial access closures.

In certain embodiments, the applicators of the invention can be used to prepare and apply a hydrogel formulation. In certain embodiments, the hydrogel formulation is delivered in liquid form and quickly polymerizes into a hydrogel. In certain embodiments, the hydrogel formulation comprises a cross linker (such as PEI); an activated polymer (such as activated PEG); and a buffer solution or solutions.

One aspect of the invention relates to a device which incorporates several separate receptacles for placing various formulation components. The various components are separate and remain stable during their intended shelf life. These receptacles are segregated into groups by various functions especially when used in reactive chemistry systems as described herein. In certain embodiments, these multiple separate receptacles can be grouped from back of the applicator towards the front of the applicator in terms of which materials must be mixed first in order to assemble correctly the formulation for ultimate delivery. The most proximal receptacle(s) are then engaged by a power source and move towards the front (distal) end of the applicator. Once engaged into the back end of the next distal receptacle, an internal plunger then is forced forward which expels the contents of the proximal receptacle into the next distal receptacle. A gate or lock-out prevents the system from engaging more distal receptacles.

Figure 11:
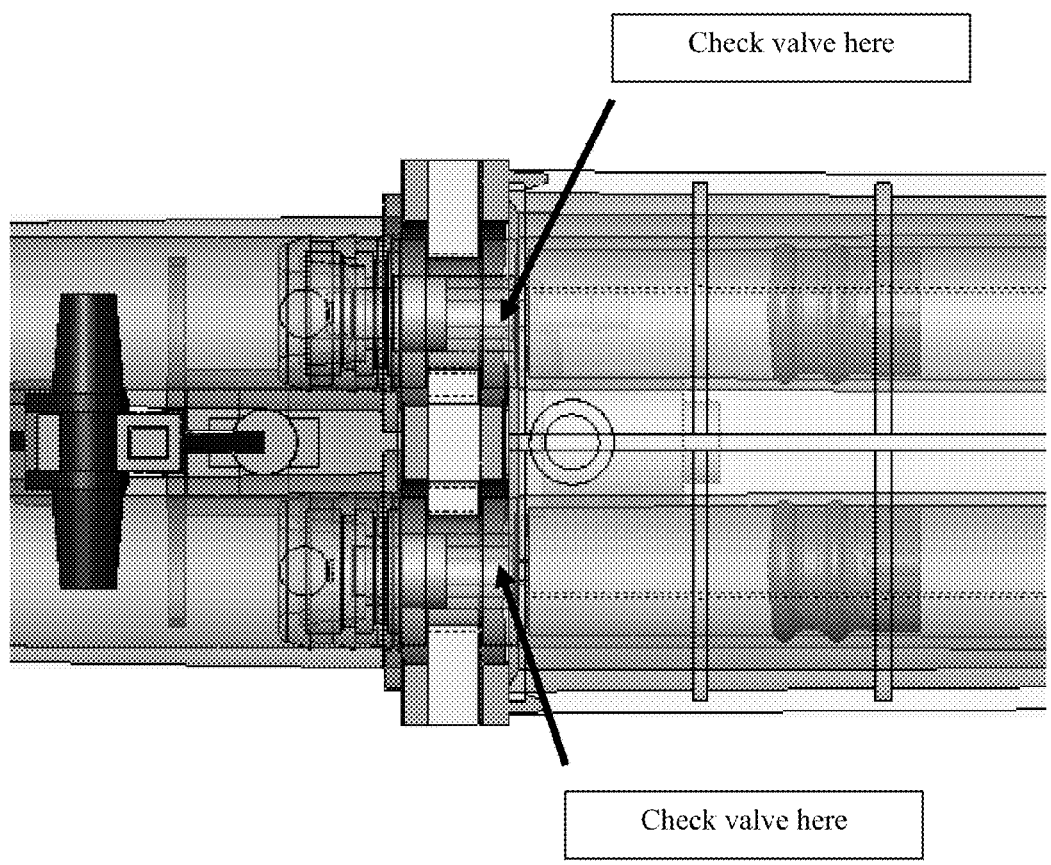

In certain embodiments of the invention, a check valve is inserted within the fluid flow path between a distal and a proximal receptacles. See, for example, FIG. 11. In certain embodiments, the check valves allow fluid flow in the direction from the buffer carriers (back of gun) towards the PEG and PEI reservoirs (front of gun). The check valves prevent fluid flow backward towards the buffer carriers. In certain embodiments, the check values are small duckbill valves. In other embodiments, the check valves are caged ball type check valves, umbrella valves or some other type of check valves.

For example, the lock-out could be a stamped flat piece of plastic that will prevent the inadvertent triggering of the internal plunger. In another embodiment, the lock-out could be a pin (such as in a grenade) that would, for example, keeps the gas bottle (or the like) from being engaged and pressurizing the applicator.

Once the gate or lock-out is activated the system can be re-energized and can continue to engage more distal receptacles. This serial engagement of a power source, engagement of a more distal receptacle and expulsion of the material in the more proximal receptacle can occur in a series of steps until the desired formulation is "reconstituted".

In addition, in other embodiments, similar groups of receptacles can be added in parallel to build a reactive system which is "reconstituted" in the first set of power engagements, but is not fully mixed for final reaction until the very last engagement of the power source at the most distal end of the applicator, whereupon the mixed formulation exits the applicator. Therefore the possible configurations become a two-dimensional matrix of possible receptacle configurations. Starting with a single part formulation with more than one constituent (for example 2, 3, 4 or more constituents) and progressing to a two part formulation with two groups of receptacles each group with more than one constituent to a three part formulation with three groups of receptacles, etc. The system is completely scalable in both dimensions for number of part constituents and for numbers of parts of the formulation (or groups of receptacles).

As used herein, the term "reconstitution" means the mixing of more than one component into a formulation or formulation part which is at least meta-stable for some indeterminate amount of time. It also includes dissolution (i.e., the process in which one substance is dissolved in another.) In certain embodiments, the individual components may not be stable in the "reconstituted" state or may suffer from other difficulties such as tolerance to sterilization procedures which makes it necessary for the components to be separate during the bulk of the storage time of the device but allow for it to be "reconstituted" into a formulation or formulation part prior to application.

In addition, while certain aspects of the invention have just been described as containing a series of receptacles for constituents which mix starting at the proximal end and working towards the distal end of the applicator, and exit through the most distal end of the applicator, alternative arrangements of components are also envisioned. In particular, it is understood by those skilled in the art that it would be possible to build applicators such that they mix from the distal end of the device and progresses toward the proximal end. In such an applicator, a fluid pathway would be constructed to convey the formulation or formulation parts back towards the distal end of the device for discharge onto the surface being treated.

In certain embodiments, the arrangement of constituent receptacles must be housed within an applicator body. This body can have any of several form factors. For example, the applicator can be shaped like a gun with a pistol style grip or it may be shaped as a pen or any number of other form factors.

Further, there are many different power sources which can be used to effect the reconstitution and expelling of the mixed formulation. These include, for example, compressed gas, mechanical power (such as compressed springs), electrical power, chemical power (such as acid and $NaHCO_3$), etc. In certain embodiments, the chosen power source can be engaged by use of a trigger, a button or other means.

In certain embodiments, the final output of the device can either deliver a stream of mixed formulation or a spray of mixed formulation.

In certain embodiments, devices of the invention can be fitted with a mixing nozzle such that it could deliver a stream of mixed formulation to a particular area. It is also contemplated that the nozzle be adapted to pass through an endoscopic or laparoscopic (and thereby could be added for use in minimally invasive surgery).

In certain embodiments, e.g., by changing the orifice size and pressure regulation of the drive train and atomization pathways, one can optimize spray capability and reduce the delivery rate of adhesive. In addition, by changing the orifice shape, one can optimize spray patterns.

In certain embodiments, precision orifices may be used to optimize the delivery rate of adhesive. For example, precision orifices can be inserted in the fluid delivery path of the nozzle prior to the area where atomization occurs (see FIG. 10). In certain embodiments, the precision orifices have a diameter in the range of about 0.001" to about 0.10". In certain embodiments, the precision orifices have a diameter in the range of about 0.002" to about 0.020". In certain embodiments, the precision orifices have a diameter in the range of about 0.004" to about 0.010".

In certain embodiments, fitments may be added to the tip of a spray applicator in order to give the applicator additional functionality above that possible with a traditional spray application system. While the general definition of "fitment" is any accessory attached to a machine, as used herein, a fitment refers to an accessory attached to the dispensing end of an applicator (i.e., the outlet).

For some applications, there is a need to limit the spray pattern to a more narrow range than initially possible for a normal air assisted spray applicator. For example, a Micromedics spray applicator will spray a swath approximately 2.5 inches in width when held 2.75 inches from the surface of the area to be sprayed. Remarkably, when a simple tube (a type of fitment) is attached to the front of the Micromedics air assisted applicator, a change in the spray pattern is noticed. In addition, it is disclosed herein that the length of the tube has a large effect on the spray pattern. In certain experiments, a tube of approximately 0.3 inches in length reduced the spray pattern to 0.9 inches wide whereas a tube of approximately 0.6 inches in length resulted in the spray coalescing within the tube and thus expelling out of the tube in the form of a discontinuous stream (when held 2.75 inches from the surface of the area to be sprayed). So thus by careful selection of tube length, a reduced width spray pattern may be accomplished. A reduced spray pattern is desirable in several applications in order to limit the spraying of unintentional areas. For example, in the spray application for dural repair, the inadvertent application of formulation on the exposed cranium is highly desired. In certain embodiment, the fitment may be easily attached and detached from the air assisted spray applicator means that the device is easily configured for a broad spray (without fitment) or a reduced width spray pattern with fitment as needed by the physician user.

Figure 9:
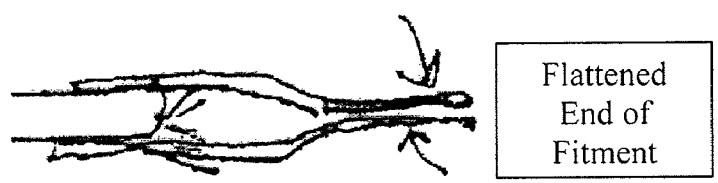
Figure 9:
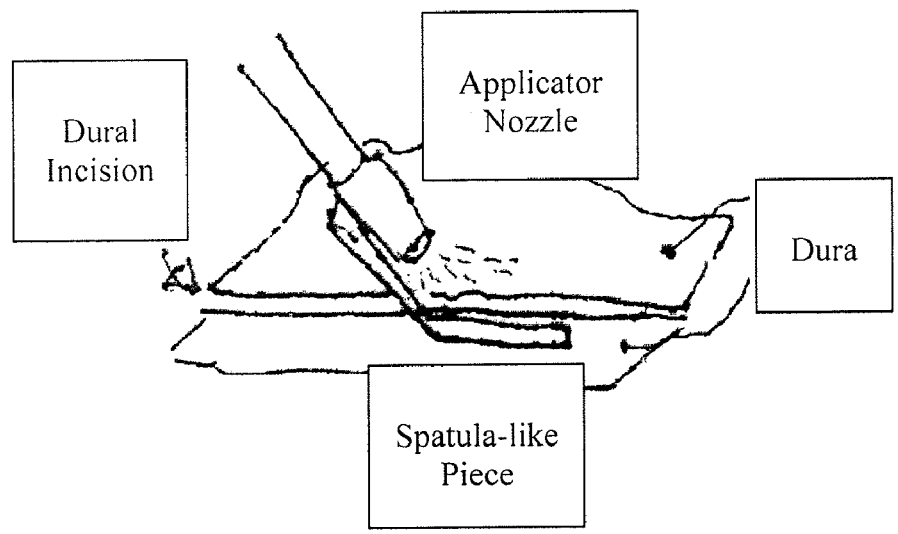
Figure 10:
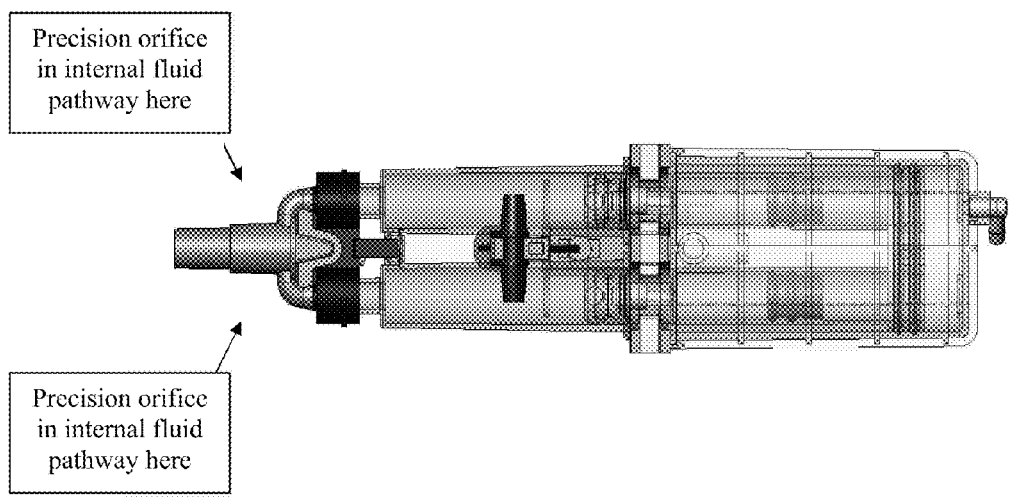

In addition, there may be times in which a user (e.g., a physician) may find it more desirable to deliver the formulation in the form of a stream rather than a spray. The concept of offering an easily detachable fitment can be used to meet this user need. One example is the closure of the dura immediately after brain surgery. In many cases, the dura has been cut and reflected back in order to allow the surgeon access to the brain for the removal of a tumor, other such brain surgery. During the time of the brain surgery, while the dura has been cut and reflected back, the dura itself often tie shrinks such that when closed, the opposite edges of dura no longer are in close approximation and many times have a gap up to 4 mm or so. In these cases, a spray application of formulation can not close the gap. By placing a tubular fitment with a flattened distal aspect onto an air assisted applicator, a stream of gelling formulation can then be applied to the surface such that the gel overlays the gap and the edges of dural tissue such that a water tight seal may be accomplished. See FIG. 9A. This is impossible to do with a traditional spray applicator.

In other embodiments, the spray applicator has a spatula-like attachment which protrudes from the distal tip of the spray applicator. In use, the spatula-like attachment is placed under the dura such that when the spray applicator is engaged, the sprayed formulation strikes the dural tissue and the spatula-like attachment under the gap within the loosely approximated dura. See FIG. 9B. As the formulation gels, the spray applicator can be advanced and the gel will dislodge from the spatula surface and remain attached to the opposing sides of the dural incision. This process can be repeated as necessary, advancing along the dural incision until the entire incision is closed.

In certain embodiments, the attachments described above may be able to be used in combination with each other for even more utility.

Polyalkyleneimine Hydrogels

In one aspect of the present invention relates to applicators for polyalkyleneimine hydrogels, and methods for using such applicators. Polyalkyleneimine hydrogels can be prepared by reacting a polyalkyleneimine (PAI) with a cross-linking agent, such as an activated polyethylene glycol. Polyalkyleneimine hydrogels are amenable to a variety of clinical treatments, such as incisions created during general surgery or wounds/incisions in the dura created during neurosurgery. Polyalkyleneimine hydrogels offer the advantage that the secondary and tertiary amino groups of the gel can be converted to secondary and tertiary ammonium cations which may encourage cell attachment and cell ingrowth. In certain instances, the secondary and tertiary amines of the polyethyleneimine (PEI) can be converted to ammonium cations by placing the PEI in an aqueous solution.

Polyalkyleneimine (PAI) hydrogels are known to have superior adhesion properties. Their superior tissue-adhesion properties may be due to two factors. First, the cationic properties of PEI promote interaction with, and possibly penetration within, an anionic tissue substrate. See Rep. Prog. Phys. 1998, 61, 1325-1365. Cationic interactions could occur through the secondary and tertiary ammonium cations of the PEI backbone or through primary amino groups that did not react with the cross-linking reagent. Second, PEI contains a large number of functional groups per molecule, thus promoting an increased number of crosslinkable sites within the polymer network. The increased number of crosslinkable sites within the polymer network affords dense, interpenetrating networks between the hydrogel and the tissue surface. The number of free amino groups in the hydrogel can be controlled by varying the ratio of PEI to activated PEG. The ability to control the number of free amino groups is significant because greater cell ingrowth was observed in tissue ingrowth experiments using hydrogels that contained a larger percentage of PEI.

In addition to increased adhesion, it has been found that as the molecular weight of the PEI increases from about 1,300 to about 2,000 g/mol the swelling of the resulting hydrogel decreases in certain instances. Thus, the molecular weight of the PEI may be adjusted in order to tune the swelling-effects of the resultant hydrogel.

A large variety of PAI derivatives are amenable to the present invention. For example, the amino groups of the PAI may be functionalized with a fatty acid, lower alkyl, an alkenyl, or alkynyl group. In addition, the amino groups or a portion of the amino groups may be functionalized to contain active agents, pharmaceutical agents, preservatives, radio isotopic ions, magnetically detectable ions, antibodies, medical contrast agents, colorants, dyes, or other visualization agents. In certain instances, about 1% to about 70% of the primary amines of the PEI are functionalized. The PAI derivatives may contain hydrolytically and/or enzymatically degradable linkages capable of releasing the functional derivatives, active agents, pharmaceutical agents, preservatives, radio isotopic ions, magnetically detectable ions, antibodies, colorants, dyes, or other visualization agents. Alternatively, a different nucleophile can be added to the PEI, such as a cysteine, isocysteine, thiol, or other such nucleophilic group. For example, a PEI can be modified such that all the primary amines are modified with a cysteine thus affording a PEI derivative which can form crosslinked gel/networks using the amine, thiol, or both the amine and thio. In certain instances, an ureido, urea, acetoacetoxy, RGD peptide, EDTA, or carbohydrate group may be bonded to one or more of the amino groups of the PEI. Representative carbohydrates include erythrose, threose, ribose, arabinose, xylose, lyxose, allose, altrose, glucose, mannose, gulose, idose, galactose, talose, sucrose, lactose, and the like. It is possible that the ureido group and urea group will impart adhesion partially via a cation/anion interaction. The acetoacetoxy group may adhere to tissue by making a metal complex on the surface of the tissue.

In certain instances, the PEI is functionalized so that both primary amino ($—NH_2$) groups and thiol ($—SH$) groups could react with electrophilic groups or a combination of them, such as an acrylate, succinimidyl ester, maleimide, ester, or aldehyde. The electrophilic groups can be attached to poly(alkyleneoxide) (e.g., PEG, PPG or PEG-PPG) polymers. Two or more electrophilic groups are required. Of course, the degree of PEI functionalization may be varied in order to obtain the desired physical properties of the resultant gel. In certain instances, only about 1% of the primary amino groups of the PEI are functionalized. In other instances, about 5% to about 25% of the primary amino groups of the PEI are functionalized. In other instances, about 25% to about 50% of the primary amino groups of the PEI are functionalized. In other instances, about 99% of the primary amino groups of the PEI are functionalized. In certain instances, one or more of the amino groups are reacted with an epoxide or acylating agent. In certain instances, one or more of the amino groups are reacted with an isocyanate.

The molecular weight of the PEI may be adjusted to tune the physical properties of the gel formed by addition of the cross-linking agent. In certain instances, the PEI has a weight average molecular weight of about 400 g/mol to about 2,000,000 g/mol. In certain instances, the PEI has a weight average molecular weight of about 400 g/mol to about 1,000,000 g/mol. In certain instances, the PEI has a weight average molecular weight of about 400 g/mol to about 500,000 g/mol. In certain instances, the PEI has a weight average molecular weight of about 400 g/mol to about 100,000 g/mol. In certain instances, the PEI has a weight average molecular weight of about 400 g/mol to about 50,000 g/mol. In certain instances, the PEI has a weight average molecular weight of about 400 g/mol to about 10,000 g/mol. In certain instances, the PEI has a weight average molecular weight of about 400 g/mol to about 5,000 g/mol. In certain instances, the PEI has a weight average molecular weight of about 400 g/mol to about 2,000 g/mol.

In certain instances, the polyalkyleneimine has a weight average molecular weight of about 600 to about 10,000 Daltons, the polyalkylene glycol has a weight average molecular weight of about 500 to about 20,000 Daltons, and the molar ratio of the polyalkyleneimine to the polyalkylene glycol is within a molar range of about 0.025:1 to about 0.4:1. In certain instances, the hydrogel reaches equilibrium swelling in about 5 to about 30 hours. In certain instances, the hydrogel reaches equilibrium swelling in about 18 hours.

In certain instances, the aforementioned polyalkyleneimine/polyalkylene glycol hydrogels may be used or modified to non-covalently carry or contain active agents, pharmaceutical agents, preservatives, radio isotopic ions, magnetically detectable ions, antibodies, medical contrast agents, colorants, dyes, or other visualization agents.

Many prior sealant systems are not optimal because the sealant system may degrade before appreciable healing or tissue ingrowth occurs. For example, tissue ingrowth often begins within one week after application of the sealant, and complete tissue ingrowth may occur within 28 days after application of the sealant in very porous systems. However, many prior sealant systems contain degradable linkages which can cause the hydrogels to degrade before appreciable tissue ingrowth occurs. While use of these materials alone is not advantageous, these materials may be used as masking materials. Accordingly, in certain instances, when polyalkyleneimine hydrogel are used as covering materials the covering can maintain its mechanical strength for at least about 7 days. In certain instances, the polyalkyleneimine hydrogel sealants of the invention maintain mechanical strength for at least about 20 days. This rate of degradation allows the masking material to degrade, while keeping the covering material in place.

Since charged species encourage tissue growth, polyalkyleneimines as masking material are advantageous because they allow for incorporation of a large number of charged species. The charged species are created by converting unreacted primary amines, and internal secondary and tertiary amines into ammonium cations under physiological conditions. Table 1 below illustrates the number of primary, secondary and tertiary amines contained in various crosslinkers based on a polymer system having eighteen primary amines. As illustrated in Table 1, the trilysine crosslinker contains only primary amines and a pendant carboxylate while a PPI (DAB)-G1 dendrimer adds 9 units of potential cationic charge with the addition of 9 tertiary amines. The PEI$_{800}$ adds 14 units of potentially charged species (i.e., 155% more charge) compared to the PPI(DAB)-G1 dendrimer, while the PEI$_{2000}$ adds 26% more potentially charged species than PEI$_{800}$. Finally, PEI$_{25000}$ adds 24% more potentially charged species than PEI$_{2000}$, owing to the increased number of secondary and tertiary amines. Since the number of secondary and tertiary amino groups increases with increasing molecular weight of the polyalkyleneimine, the polyalkyleneimine hydrogels of the invention can be tuned by incorporating crosslinkers with varying molecular weights, and hence charge density, in order to affect the tissue ingrowth and degradation properties of the hydrogel.

TABLE 1

| Crosslinker | 1° amines | 2° amines | 3° amines |
| --- | --- | --- | --- |
| PEI$_{25000}$ | 18 | 22 | 14 |
| PEI$_{2000}$ | 18 | 17 | 12 |
| PEI$_{800}$ | 18 | 14 | 9 |
| PPI(DAB)-G1 | 18 | 0 | 9 |
| Trilysine | 4 | 0 | 0 |

Again, when used as masking material, polyalkyleneimine hydrogel sealants offer an advantage over prior sealant systems because polyalkyleneimines, especially derivatized polyalkyleneimines, should have antimicrobial and antiviral activity. Recent reports indicate that both polyalkyleneimines and derivatives thereof have antimicrobial properties, while lacking activity against mammalian cells. See *Biotechnol. Bioeng.* 2005, 90, 715-722; *Biotechnol. Bioeng.* 2003, 83, 168-172; *Biotechnology Letters* 2003, 25, 1661-1665; *Biotechnol. Prog.* 2002, 18, 1082-1086; *Chem. Commun.* 1999, 1585-1586; and *Proc. Nat. Acad. Sci. USA* 2006, 103, 17667-17671. Thus, hydrogels prepared from polyalkyleneimines may help fight, inhibit, prevent or even eliminate the chance for infection when applied to the tissue of a patient. Since the presence of cationic groups, especially quaternary amines, may influence the antimicrobial properties of the hydrogel, the PAI, in certain instances, may be derivatized with one or more quaternary amines. In certain instances, the PAI may be derivatized with four or more quaternary amines. In certain instances, the PAI may be derivatized with ten or more quaternary amines. Since the presence of cationic groups and hydrophobic side chains, when combined, tend to confer better antimicrobial properties, the PAI, in certain instances, may be derivatized with one or more quaternary amines and one or more fatty acid, lower alkyl, alkenyl, or alkynyl groups.

Polyalkyleneimine hydrogels offer the additional advantage that the amino groups of the polyalkyleneimine can act as a buffering agent. The ability to control the pH during preparation of the hydrogel is important because certain pHs are optimal for crosslinking of the components. In particular, the pH of a mixture of crosslinking components can affect the rate at which the crosslinking reaction takes places. In some instances, the desired pH can be achieved by adding a buffering agent, such as phosphates, carbonates, borates, and the like, to the solution containing the crosslinking components. However, when using poly alkyleneimines as a crosslinkable component, the primary, secondary, and tertiary amines act as buffering agents to provide some buffering capacity throughout a wide range of pHs. See *Bioorganic Chemistry* 1994, 22, 318-327. Moreover, as the crosslinkable component reacts, some of the amines are removed from solution, thereby reducing the pH. Since quick set-times can require higher pHs, it is advantageous to use a crosslinkable component which influences the pH so that the pH will lower to more physiological levels soon after mixing. This buffering feature of polyalkyleneimines eliminates the need for a strong buffer to achieve the high pH-levels sometimes used in preparing a hydrogel. Notably, addition of strong buffers may not be desirable because such buffers may remain in the sealant and cause the patient's tissue to become irritated.

As mentioned above, in certain embodiments the applicators of the invention may be configured to react polyalkyleneimines, or other amine-containing polymers, with cross-linking agents, to form hydrogels. A large number of cross-linking agents are amenable to the invention. In certain instances, the cross-linking agent is an activated polyethylene glycol. The activating group is preferably an electrophilic group. For example, in certain instances, the polyethylene glycol contains a N-hydroxysuccinimide group at each end of the polymer. In certain instances, the succinimide is functionalized with a sulfonic acid moiety. In certain instances, the polyethylene glycol contains an aldehyde at each end of the polyethylene glycol. In certain instances the polyethylene glycol is a star, dendritic, or branched polymer with three or more activating groups.

In certain instances, the polyethylene glycol cross-linking agent contains two or more different electrophiles. The different electrophiles may have similar or dissimilar reactivities. The different electrophiles provide linkages having similar or dissimilar degradation rates. The selection of electrophiles allows for control over the crosslinking reactions to form the hydrogels, the adhesive properties, and the degradation rate of the formed hydrogel. For example, a polyethylene glycol can be derivatized such that one end of the polyethylene glycol contains a SPA and another end contains a SG. In this example, both are activated esters, but the degradation rates of the two linkages are different. For example, a hydrogel prepared with only a PEG-SPA is generally stable at 37° C. for more than about four months, whereas a hydrogel prepared with PEG-SG is often stable for less than about one week. Notably, one hydrogel prepared from PEI and a PEG-SPA/SG having a 60:40 ratio of SPA:SG degraded in about a week.

In certain instance, more than one polyethylene glycol cross-liking agents can be used. For example, a mixture of PEI/PEG-SPA and PEI/PEG-SG. The different cross-linkers may provide linkages having similar or dissimilar degradation rates, and thus the properties of the resulting hydrogel can be controlled.

In certain instances, the polyethylene glycol cross-linking agent contains a hydrophobic moiety. In certain instances, alkyl groups are installed between the polyethylene glycol and the terminal electrophilic groups of the cross-linking agent. In certain instances, the alkyl group contains about 4 to about 30 carbon atoms. In certain instances, the alkyl group contains about 5 to about 15 carbon atoms. In certain instances, the hydrophobic moiety is an aryl or aralkyl group. In certain instances, the alkyl moiety of the aralkyl group contains between 5-10 carbon atoms.

In certain instances, the polyethylene glycol cross-linking agent is represented by the generic formula (i) below, wherein w is an integer in the range of about 5 to 10,000, and n is an integer in the range of about 5 to about 30.

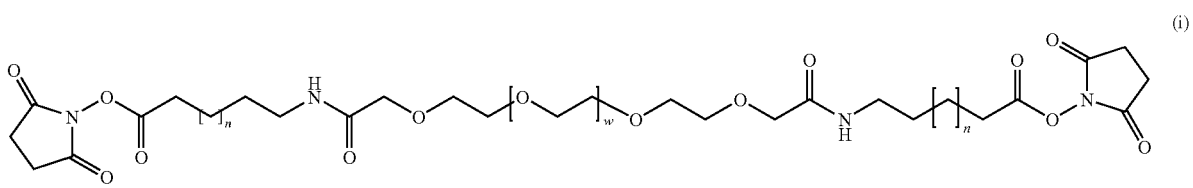
(i)

In certain instances, the polyethylene glycol cross-linking agent is represented by the generic formula (ii) below, wherein w is an integer in the range of about 5 to 10,000, and m is an integer in the range of about 1 to about 50.

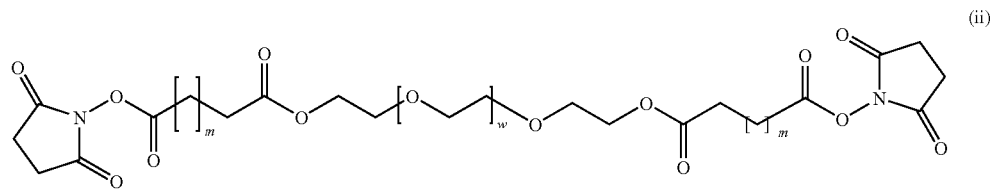
(ii)

In certain instances the hydrophobic moiety may be used as a foaming agent. The linkages between the polyethylene glycol and the hydrophobic moiety can be esters, amides, carbamates, carbonates, urea, urethane, and so forth.

A further embodiment of this invention is an applicator, and methods of use thereof, for chemical peptide ligation reactions, to create a crosslinked gel involving a dendritic polymer. In this reaction an aldehyde, aldehyde-acid or aldehyde-ester reacts with a cysteine-functionalized polymer to form a gel or crosslinked network. In certain instances, the dendritic polymers have nucleophilic groups, such as primary amino groups or thiol groups, which can react with electrophilic groups, such as an acrylate, succinimidyl ester, maleimide, ester aldehyde, or aldehyde on a small molecule. In certain instances, the dendritic polymer has nucleophilic groups capable of reacting with an activated diester of sebacic acid.

Selected Applicators

One aspect of the invention relates to an applicator, comprising a rear housing, a front housing, a mechanical interlock and a nozzle assembly; wherein (i) the rear housing comprises:
a first barrel, having a first diameter; a first end; a second end; a first internal chamber; a first piercer, attached to the second end of the first barrel, having a first fluid passageway; and a first plunger, having a first end and a second end, located at least partially within the first internal chamber and under pressure moveable therethrough; and
a second barrel having a second diameter; a first end; a second end; a second internal chamber; a second piercer, located on the second end of the second barrel, having a second fluid passageway; and a second plunger, having a first end and a second end, located at least partially within the second internal chamber and under pressure moveable therethrough;

(ii) the front housing comprises:
a third barrel, having a third diameter; a first end; a second end; a third internal chamber; a first piston having a third fluid passageway therethrough, located within the third internal chamber and under pressure moveable therethrough; a first piercable barrier, located at the first end of the third barrel and suitably positioned to be pierced by the first piercer, thereby allowing fluid communication between the first internal chamber and the second internal chamber via the first fluid passageway and the third fluid passageway; and a second piercable barrier, located at the second end of the third barrel; and
a fourth barrel, having a fourth diameter; a first end; a second end; a fourth internal chamber; a second piston having a fourth fluid passageway therethrough, located within the fourth internal chamber and under pressure moveable therethrough; a third piercable barrier, located at the first end of the fourth barrel and suitably positioned to be pierced by the second piercer, thereby allowing fluid communication between the second internal chamber and the fourth internal chamber via the second fluid passageway and the fourth fluid passageway; and a fourth piercable barrier, located at the second end of the fourth barrel; and (iii) the nozzle assembly comprises:
a fifth internal chamber; having a first inlet with a third piercer affixed thereto, which comprises a fifth fluid passageway, and is suitably positioned at the first inlet to pierce the second piercable barrier and thereby allow fluid communication between the third internal chamber and the fifth internal chamber via the fifth fluid passageway; a second inlet with a fourth piercer affixed thereto, which comprises a sixth fluid passageway, and is suitably positioned at the second inlet to pierce the fourth piercable barrier and thereby allow fluid communication between the fourth internal chamber and the fifth internal chamber via the sixth fluid passageway; and an outlet;

wherein the nozzle assembly is connected to the front housing; the front housing is connected to the rear housing; the first diameter is less than the third diameter; the second diameter is less than the fourth diameter; the first piercer is sized to block the first fluid passageway; the second piercer is sized to block the second fluid passageway; and the mechanical interlock is positioned to allow initially the first piercer to pierce the first barrier but not block the first fluid passageway; and the mechanical interlock is positioned to initially allow the second piercer to pierce the second barrier but not block the second fluid passageway.

In certain embodiments, the present invention relates to any one of the aforementioned applicators, wherein the applicator body further comprises a liquid in the first internal chamber.

In certain embodiments, the present invention relates to any one of the aforementioned applicators, wherein the applicator body further comprises a liquid in the first internal chamber; and the applicator has a sterility assurance level of between about $10^{-3}$ to about $10^{-6}$.

In certain embodiments, the present invention relates to any one of the aforementioned applicators, wherein the applicator body further comprises a liquid in the first internal chamber; and the liquid is a buffer.

In certain embodiments, the present invention relates to any one of the aforementioned applicators, wherein the applicator body further comprises a liquid in second internal chamber.

In certain embodiments, the present invention relates to any one of the aforementioned applicators, wherein the applicator body further comprises a liquid in the second internal chamber; and the applicator has a sterility assurance level of between about $10^{-3}$ to about $10^{-6}$.

In certain embodiments, the present invention relates to any one of the aforementioned applicators, wherein the applicator body further comprises a liquid in the second internal chamber the liquid is a buffer.

In certain embodiments, the present invention relates to any one of the aforementioned applicators, wherein the applicator body further comprises a solid in the third internal chamber.

In certain embodiments, the present invention relates to any one of the aforementioned applicators, wherein the applicator body further comprises a solid in the third internal chamber; and the applicator has a sterility assurance level of between about $10^{-3}$ to $10^{-6}$.

In certain embodiments, the present invention relates to any one of the aforementioned applicators, wherein the applicator body further comprises a solid in the third internal chamber; and the solid comprises a polyalkyleneimine.

In certain embodiments, the present invention relates to any one of the aforementioned applicators, wherein the applicator body further comprises a viscous liquid in the third internal chamber; and the viscous liquid comprises PEI. In certain embodiment, the PEI, or other viscous liquid component, may be dissolved in a small amount of solvent (e.g., water or buffer) to aid in the reconstituting.

In certain embodiments, the present invention relates to any one of the aforementioned applicators, wherein the applicator body further comprises a solid in the fourth internal chamber.

In certain embodiments, the present invention relates to any one of the aforementioned applicators, wherein the applicator body further comprises a solid in the fourth internal chamber; and the applicator has a sterility assurance level of between about $10^{-3}$ to $10^{-6}$.

In certain embodiments, the present invention relates to any one of the aforementioned applicators, wherein the applicator body further comprises a solid in the fourth internal chamber; and the solid comprises a $PEG(NHS)_2$ or a mixture of two or more $PEG(NHS)_2$.

In certain embodiments, the present invention relates to any one of the aforementioned applicators, wherein the applicator body further comprises a solid in the fourth internal chamber; and the solid comprises

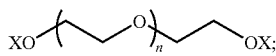

wherein n is 10-200 inclusive; and X is —$CH_2C(=O)O(N$-succinimidyl), —$(CH_2)_2C(=O)O(N$-succinimidyl), —$(CH_2)_3C(=O)O(N$-succinimidyl), —$(CH_2)_4C(=O)O(N$-succinimidyl), —$(CH_2)_5C(=O)O(N$-succinimidyl), —$(CH_2)_6C(=O)O(N$-succinimidyl), —$(CH_2)_7C(=O)O(N$-succinimidyl), —$(CH_2)_8C(=O)O(N$-succinimidyl), —$(CH_2)_9C(=O)O(N$-succinimidyl), —$C(=O)CH_2C(=O)O(N$-succinimidyl), —$C(=O)(CH_2)_2C(=O)O(N$-succinimidyl), —$C(=O)(CH_2)_3C(=O)O(N$-succinimidyl), —$C(=O)(CH_2)_4C(=O)O(N$-succinimidyl), —$C(=O)(CH_2)_5C(=O)O(N$-succinimidyl), —$C(=O)(CH_2)_6C(=O)O(N$-succinimidyl), —$C(=O)(CH_2)_7C(=O)O(N$-succinimidyl), —$C(=O)(CH_2)_8C(=O)O(N$-succinimidyl), or —$C(=O)(CH_2)_9C(=O)O(N$-succinimidyl).

In certain embodiments, the present invention relates to any one of the aforementioned applicators, wherein the applicator body further comprises a solid in the fourth internal chamber; and the solid is

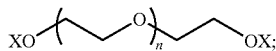

wherein n is 80-120 inclusive; and X is —$(CH_2)_3C(=O)O(N$-succinimidyl), —$C(=O)(CH_2)_3C(=O)O(N$-succinimidyl), or —$C(=O)(CH_2)_8C(=O)O(N$-succinimidyl).

In certain embodiments, the present invention relates to any one of the aforementioned applicators, wherein the third internal chamber is under partial.

In certain embodiments, the present invention relates to any one of the aforementioned applicators, wherein the fourth internal chamber is under partial vacuum.

In certain embodiments, the present invention relates to any one of the aforementioned applicators, further comprising a check valve between the first fluid passageway and the third fluid passageway; and further comprising a check valve between the second fluid passageway and the fourth fluid passageway.

In certain embodiments, the present invention relates to any one of the aforementioned applicators, wherein the check valve is a duckbill valve, a caged ball type check valve or an umbrella valve.

In certain embodiments, the present invention relates to any one of the aforementioned applicators, wherein the check valve is a duckbill valve.

In certain embodiments, the present invention relates to any one of the aforementioned applicators, wherein the nozzle further comprises two precision orifices; the fifth fluid passageway pass through one of said orifices; and the sixth fluid passageway pass through the other of said orifices.

In certain embodiments, the present invention relates to any one of the aforementioned applicators, wherein the precision orifices each have a diameter between about 0.002" and about 0.020".

In certain embodiments, the present invention relates to any one of the aforementioned applicators, wherein the precision orifices each have a diameter between about 0.004" and about 0.010".

In certain embodiments, the present invention relates to any one of the aforementioned applicators, wherein the nozzle further comprises a brush, a sponge, a foam swab, a porous plastic component, a duck bill tip, a textile mitt or a spray tip affixed to the outlet.

In certain embodiments, the present invention relates to any one of the aforementioned applicators, wherein the nozzle further comprises a tubular fitment having two open ends; one end of the tubular fitment is affixed to the outlet; and the tubular fitment is adapted to pass through an endoscope or a laparoscope.

In certain embodiments, the present invention relates to any one of the aforementioned applicators, wherein the nozzle further comprises a tubular fitment having two open ends; one open end of the tubular fitment is affixed to the outlet and the other open end of the fitment has a flattened opening relative to the open end affixed to the outlet.

In certain embodiments, the present invention relates to any one of the aforementioned applicators, wherein the nozzle further comprises a tubular fitment having two open ends; one open end of the tubular fitment is affixed to the outlet and the other open end of the fitment comprises a protruding spatula-like piece.

In certain embodiments, the present invention relates to any one of the aforementioned applicators, wherein said applicator is shaped like a pen.

In certain embodiments, the present invention relates to any one of the aforementioned applicators, wherein said applicator is shaped like a gun.

In certain embodiments, the present invention relates to any one of the aforementioned applicators, wherein said applicator is shaped like a gun; and the applicator further comprises a pistol-style grip.

In certain embodiments, the present invention relates to any one of the aforementioned applicators, further comprising an atomization fluid pathway.

In certain embodiments, the present invention relates to any one of the aforementioned applicators, further comprising an atomization fluid pathway; wherein said atomization fluid pathway is configured to expel any material in the fifth internal chamber out of the nozzle through the outlet.

In certain embodiments, the present invention relates to any one of the aforementioned applicators, further comprising a drive train fluid pathway.

In certain embodiments, the present invention relates to any one of the aforementioned applicators, wherein said applicator further comprises a trigger mechanism which controls the movement of one or more plungers or pistons.

In certain embodiments, the present invention relates to any one of the aforementioned applicators, wherein said applicator further comprises a trigger mechanism which controls the movement of one or more plungers or pistons; and the trigger comprises a linear two-stage valve.

In certain embodiments, the present invention relates to any one of the aforementioned applicators, wherein said applicator further comprises a trigger mechanism which controls the movement of one or more plungers or pistons and a lockout mechanism which prevents inadvertent engagement of the trigger; and the trigger comprises a linear two-stage valve.

In certain embodiments, the present invention relates to any one of the aforementioned applicators, wherein said applicator further comprises a trigger mechanism which controls the movement of one or more plungers or pistons and a lockout mechanism which prevents inadvertent engagement of the trigger; the trigger comprises a linear two-stage valve; and the lockout mechanism comprises a stamped flat piece of plastic.

In certain embodiments, the present invention relates to any one of the aforementioned applicators, further comprising an atomization fluid pathway, a drive train fluid pathway, and a trigger mechanism which controls the movement of one or more barrels, plungers or pistons; wherein the trigger comprises a linear two-stage valve; the first stage of the valve is connected to an atomization fluid pathway; and the second stage of the valve is connected to a drive train fluid pathway.

In certain embodiments, the present invention relates to any one of the aforementioned applicators, wherein said applicator further comprises a trigger mechanism which controls the movement of one or more plungers or pistons; and the trigger comprises a linear two-stage valve, and can be mechanically or manually pushed forward to de-energize the applicator.

In certain embodiments, the present invention relates to any one of the aforementioned applicators, wherein said applicator further comprises a trigger mechanism which controls the movement of one or more plungers or pistons; and the trigger comprises a button.

In certain embodiments, the present invention relates to any one of the aforementioned applicators, wherein said applicator further comprises a trigger mechanism which controls the movement of one or more plungers or pistons and a lockout mechanism which prevents inadvertent engagement of the trigger; and the trigger comprises a button.

In certain embodiments, the present invention relates to any one of the aforementioned applicators, wherein said applicator further comprises a trigger mechanism which controls the movement of one or more plungers or pistons and a lockout mechanism which prevents inadvertent engagement of the trigger; the trigger comprises a button; and the lockout mechanism comprises a stamped flat piece of plastic.

In certain embodiments, the present invention relates to any one of the aforementioned applicators, further comprising a power source to cause the first piercer to pierce the first piercable barrier, cause the second piercer to pierce the second piercable barrier, or both.

In certain embodiments, the present invention relates to any one of the aforementioned applicators, further comprising a power source to cause the third piercer to pierce the third piercable barrier, cause the fourth piercer to pierce the fourth piercable barrier, or both.

In certain embodiments, the present invention relates to any one of the aforementioned applicators, further comprising a power source to cause the first piston to move to the second end of the first barrel, to cause the second piston to move to the second end of the second barrel, or both.

In certain embodiments, the present invention relates to any one of the aforementioned applicators, further comprising a power source to cause the third piston to move to the second end of the third barrel, to cause the fourth piston to move to the second end of the fourth barrel, or both.

In certain embodiments, the present invention relates to any one of the aforementioned applicators, further comprising a power source; wherein said power source is contained within the applicator.

In certain embodiments, the present invention relates to any one of the aforementioned applicators, further comprising a power source; wherein said power source is outside of the applicator.

In certain embodiments, the present invention relates to any one of the aforementioned applicators, further comprising a power source; wherein said power source is selected from the group consisting of compressed gas, mechanical power, chemical power, and electrical power.

In certain embodiments, the present invention relates to any one of the aforementioned applicators, further comprising a means to use chemical power as a power source.

In certain embodiments, the present invention relates to any one of the aforementioned applicators, further comprising compressed gas as a power source.

In certain embodiments, the present invention relates to any one of the aforementioned applicators, further comprising a spring as a power source.

In certain embodiments, the present invention relates to any one of the aforementioned applicators, further comprising a means to use manual power as a power source.

In certain embodiments, the present invention relates to any one of the aforementioned applicators, wherein the first piercable barrier comprises one or more polymers selected from the group consisting of polyacrylics, silicones, polyolefins, polystyrenes, polyesters, polyethers, polyurethanes, polycarbonates, polyamines, and co-polymers thereof.

In certain embodiments, the present invention relates to any one of the aforementioned applicators, wherein the first piercable barrier comprises a metal.

In certain embodiments, the present invention relates to any one of the aforementioned applicators, wherein the exterior surface of the first piercable barrier is paper coated with wax or plastic.

In certain embodiments, the present invention relates to any one of the aforementioned applicators, wherein the second piercable barrier comprises one or more polymers selected from the group consisting of polyacrylics, silicones, polyolefins, polystyrenes, polyesters, polyethers, polyurethanes, polycarbonates, polyamines, and co-polymers thereof.

In certain embodiments, the present invention relates to any one of the aforementioned applicators, wherein the second piercable barrier comprises a metal.

In certain embodiments, the present invention relates to any one of the aforementioned applicators, wherein the exterior surface of the second piercable barrier is paper coated with wax or plastic.

In certain embodiments, the present invention relates to any one of the aforementioned applicators, wherein the third piercable barrier comprises one or more polymers selected from the group consisting of polyacrylics, silicones, polyolefins, polystyrenes, polyesters, polyethers, polyurethanes, polycarbonates, polyamines, and co-polymers thereof.

In certain embodiments, the present invention relates to any one of the aforementioned applicators, wherein the third piercable barrier comprises a metal.

In certain embodiments, the present invention relates to any one of the aforementioned applicators, wherein the exterior surface of the third piercable barrier is paper coated with wax or plastic.

In certain embodiments, the present invention relates to any one of the aforementioned applicators, wherein the fourth piercable barrier comprises one or more polymers selected from the group consisting of polyacrylics, silicones, polyolefins, polystyrenes, polyesters, polyethers, polyurethanes, polycarbonates, polyamines, and co-polymers thereof.

In certain embodiments, the present invention relates to any one of the aforementioned applicators, wherein the fourth piercable barrier comprises a metal.

In certain embodiments, the present invention relates to any one of the aforementioned applicators, wherein the exterior surface of the fourth piercable barrier is paper coated with wax or plastic.

In certain embodiments, the present invention relates to any one of the aforementioned applicators, wherein the first barrel and the second barrel are mechanically locked such that their ability to advance through the third barrel and the fourth barrel, respectively, is constrained to be substantially simultaneous.

In certain embodiments, the present invention relates to any one of the aforementioned applicators, wherein the length of the first barrel is between about 0.5 inches to about 9 inches; or about 1.5 inches to about 4 inches; or about 2 inches to about 3 inches.

In certain embodiments, the present invention relates to any one of the aforementioned applicators, wherein the diameter of the first barrel is between about 0.2 inches and about 2 inches; or about 0.3 inches to about 0.75 inches; or about 0.4 inches to about 0.6 inches.

In certain embodiments, the present invention relates to any one of the aforementioned applicators, wherein the length of the second barrel is between about 0.5 inches to about 9 inches; or about 1.5 inches to about 4 inches; or about 2 inches to about 3 inches.

In certain embodiments, the present invention relates to any one of the aforementioned applicators, wherein the diameter of the second barrel is between about 0.2 inches and about 2 inches; or about 0.3 inches to about 0.75 inches; or about 0.4 inches to about 0.6 inches.

In certain embodiments, the present invention relates to any one of the aforementioned applicators, wherein the length of the third barrel is between about 0.5 inches and about 6 inches.

In certain embodiments, the present invention relates to any one of the aforementioned applicators, wherein the diameter of the third barrel is between about 0.2 inches and about 2 inches; or about 0.3 inches to about 0.75 inches; or about 0.4 inches to about 0.6 inches.

In certain embodiments, the present invention relates to any one of the aforementioned applicators, wherein the length of the fourth barrel is between about 0.5 inches to about 6 inches; or about 1.5 inches to about 4 inches; or about 2 inches to about 3 inches.

In certain embodiments, the present invention relates to any one of the aforementioned applicators, wherein the diameter of the fourth barrel is between about 0.2 inches and about 2 inches; or about 0.3 inches to about 0.75 inches; or about 0.4 inches to about 0.6 inches.

In certain embodiments, the present invention relates to any one of the aforementioned applicators, wherein the length of the nozzle assembly is between about 0.5 inches and about 15 inches; or about 0.75 inches to about 6 inches; or about 1 inch to about 2 inches.

In certain embodiments, the present invention relates to any one of the aforementioned applicators, wherein the diameter of the outlet is between about 0.1 inches and about 1 inch.

One aspect of the invention relates to an applicator comprising an applicator body and a tubular removable fitment; wherein the tubular removable fitment has a first open end and a second open end; the first open end is attached to the applicator body; and the second open end is adapted to pass through a trocar port in a scope.

In certain embodiments, the present invention relates to any one of the aforementioned applicators, wherein the scope is an endoscope or a laparoscope.

One aspect of the invention relates to an applicator comprising an applicator body and a tubular removable fitment; wherein the tubular removable fitment has a first open end and a second open end; the first open end is attached to the applicator body; and the second open end has a flattened opening relative to the first open end.

One aspect of the invention relates to an applicator comprising an applicator body and a tubular removable fitment; wherein the tubular removable fitment has a first open end and a second open end; the first open end is attached to the applicator body; and the second open end comprises a protruding spatula-like piece.

In certain embodiments, the present invention relates to any one of the aforementioned applicators, wherein the applicator is a spray applicator for tissue adhesives or therapeutic hydrogels.

One aspect of the invention relates to a tubular removable fitment; wherein the tubular removable fitment has a first open end and a second open end; the first open end is adapted to attach to an applicator; and the second open end is adapted to pass through a trocar port in a scope.

In certain embodiments, the present invention relates to any one of the aforementioned fitments, wherein the scope is an endoscope or a laparoscope.

One aspect of the invention relates to a tubular removable fitment; wherein the tubular removable fitment has a first open end and a second open end; the first open end is adapted to attach to an applicator; and the second open end has a flattened opening relative to the first open end.

One aspect of the invention relates to a tubular removable fitment; wherein the tubular removable fitment has a first open end and a second open end; the first open end is adapted to attach to an applicator body; and the second open end comprises a protruding spatula-like piece.

Selected Methods

One aspect of the invention relates to a method of using an applicator to apply a composition to a surface;

wherein the applicator comprises a rear housing, a front housing, a mechanical interlock and a nozzle assembly; wherein (i) the rear housing comprises:
a first barrel, having a first diameter; a first end; a second end; a first internal chamber containing a first liquid; a first piercer, attached to the second end of the first barrel, having a first fluid passageway; and a first plunger, having a first end and a second end, located at least partially within the first internal chamber and under pressure moveable therethrough; and
a second barrel having a second diameter; a first end; a second end; a second internal chamber containing a second liquid; a second piercer, located on the second end of the second barrel, having a second fluid passageway; and a second plunger, having a first end and a second end, located at least partially within the second internal chamber and under pressure moveable therethrough;

(ii) the front housing comprises:

a third barrel, having a third diameter; a first end; a second end; a third internal chamber containing a first solid; a first piston having a third fluid passageway therethrough, located within the third internal chamber and under pressure moveable therethrough; a first piercable barrier, located at the first end of the third barrel and suitably positioned to be pierced by the first piercer, thereby allowing fluid communication between the first internal chamber and the second internal chamber via the first fluid passageway and the third fluid passageway; and a second piercable barrier, located at the second end of the third barrel; and a fourth barrel, having a fourth diameter; a first end; a second end; a fourth internal chamber containing a second solid; a second piston having a fourth fluid passageway therethrough, located within the fourth internal chamber and under pressure moveable therethrough; a third piercable barrier, located at the first end of the fourth barrel and suitably positioned to be pierced by the second piercer, thereby allowing fluid communication between the second internal chamber and the fourth internal chamber via the second fluid passageway and the fourth fluid passageway; and a fourth piercable barrier, located at the second end of the fourth barrel; and (iii) the nozzle assembly comprises:

a fifth internal chamber; having a first inlet with a third piercer affixed thereto, which comprises a fifth fluid passageway, and is suitably positioned at the first inlet to pierce the second piercable barrier and thereby allow fluid communication between the third internal chamber and the fifth internal chamber via the fifth fluid passageway; a second inlet with a fourth piercer affixed thereto, which comprises a sixth fluid passageway, and is suitably positioned at the second inlet to pierce the fourth piercable barrier and thereby allow fluid communication between the fourth internal chamber and the fifth internal chamber via the sixth fluid passageway; and an outlet;

wherein the nozzle assembly is connected to the front housing; the front housing is connected to the rear housing; the first diameter is less than the third diameter; the second diameter is less than the fourth diameter; the first piercer is sized to block the first fluid passageway; the second piercer is sized to block the second fluid passageway; and the mechanical interlock is positioned to allow initially the first piercer to pierce the first barrier but not block the first fluid passageway; and the mechanical interlock is positioned to initially allow the second piercer to pierce the second barrier but not block the second fluid passageway;

comprising the steps of:

advancing the first barrel towards the nozzle and into the third barrel, thereby piercing the first barrier, placing the first internal chamber in fluid communication with the third internal chamber;

advancing the first plunger towards the nozzle, thereby expelling the first liquid into the third internal chamber, forming a first mixture of the first liquid and the first solid;

advancing the second barrel towards the nozzle and into the fourth barrel, thereby piercing the second barrier, placing the second internal chamber in fluid communication with the fourth internal chamber;

advancing the second plunger towards the nozzle, thereby expelling the second liquid into the fourth internal chamber, forming a second mixture of the first liquid and the first solid;

advancing the third barrel towards the nozzle, thereby piercing the third barrier and placing the third internal chamber in fluid communication with the fifth internal chamber;

advancing the fourth barrel towards the nozzle, thereby piercing the fourth barrier, placing the fourth internal chamber in fluid communication with the fifth internal chamber;

advancing the first piston and the second piston towards the nozzle, thereby causing the first mixture to mix with the second mixture in the fifth internal chamber, forming a pre-composition mixture;

applying the pre-composition mixture to the surface, wherein the mixture gels to form the composition on the surface.

In certain embodiments, the present invention relates to any one of the aforementioned methods, further comprising agitating the applicator to promote mixing of the first liquid with the first solid; and to promote mixing of the second liquid with the second solid.

In certain embodiments, the present invention relates to any one of the aforementioned methods, wherein the composition is a hydrogel.

In certain embodiments, the present invention relates to any one of the aforementioned methods, wherein the composition is a polyalkyleneimine hydrogel.

In certain embodiments, the present invention relates to any one of the aforementioned methods, wherein the surface is dura matter, abdominal tissue, tissue adjacent to a spine, internal tissue, lung tissue, intestinal tissue, a cornea, or any internal surface.

In certain embodiments, the present invention relates to any one of the aforementioned methods, wherein the applicator body further comprises a liquid in the first internal chamber.

In certain embodiments, the present invention relates to any one of the aforementioned methods, wherein the applicator body further comprises a liquid in the first internal chamber; and the applicator has a sterility assurance level of between about $10^{-3}$ to about $10^{-6}$.

In certain embodiments, the present invention relates to any one of the aforementioned methods, wherein the applicator body further comprises a liquid in the first internal chamber; and the liquid is a buffer.

In certain embodiments, the present invention relates to any one of the aforementioned methods, wherein the applicator body further comprises a liquid in second internal chamber.

In certain embodiments, the present invention relates to any one of the aforementioned methods, wherein the applicator body further comprises a liquid in the second internal chamber; and the applicator has a sterility assurance level of between about $10^{-3}$ to about $10^{-6}$.

In certain embodiments, the present invention relates to any one of the aforementioned methods, wherein the applicator body further comprises a liquid in the second internal chamber the liquid is a buffer.

In certain embodiments, the present invention relates to any one of the aforementioned methods, wherein the applicator body further comprises a solid in the third internal chamber.

In certain embodiments, the present invention relates to any one of the aforementioned methods, wherein the applicator body further comprises a solid in the third internal chamber; and the applicator has a sterility assurance level of between about $10^{-3}$ to about $10^{-6}$.

In certain embodiments, the present invention relates to any one of the aforementioned methods, wherein the applicator body further comprises a solid in the third internal chamber; and the solid comprises a polyalkyleneimine.

In certain embodiments, the present invention relates to any one of the aforementioned methods, wherein the applicator body further comprises a solid in the third internal chamber; and the solid comprises PEI.

In certain embodiments, the present invention relates to any one of the aforementioned methods, wherein the applicator body further comprises a solid in the fourth internal chamber.

In certain embodiments, the present invention relates to any one of the aforementioned methods, wherein the applicator body further comprises a solid in the fourth internal chamber; and the applicator has a sterility assurance level of between about $10^{-3}$ to about $10^{-6}$.

In certain embodiments, the present invention relates to any one of the aforementioned methods, wherein the applicator body further comprises a solid in the fourth internal chamber; and the solid comprises a $PEG(NHS)_2$ or a mixture of two or more $PEG(NHS)_2$.

In certain embodiments, the present invention relates to any one of the aforementioned methods, wherein the applicator body further comprises a solid in the fourth internal chamber; and the solid comprises $$XO \overparen{\phantom{XX}O\phantom{XX}}_n OX;$$

wherein n is 10-200 inclusive; and X is —$CH_2C(=O)O(N$-succinimidyl), —$(CH_2)_2C(=O)O(N$-succinimidyl), —$(CH_2)_3C(=O)O(N$-succinimidyl), —$(CH_2)_4C(=O)O(N$-succinimidyl), —$(CH_2)_5C(=O)O(N$-succinimidyl), —$(CH_2)_6C(=O)O(N$-succinimidyl), —$(CH_2)_7C(=O)O(N$-succinimidyl), —$(CH_2)_8C(=O)O(N$-succinimidyl), —$(CH_2)_9C(=O)O(N$-succinimidyl), —$C(=O)CH_2C(=O)O(N$-succinimidyl), —$C(=O)(CH_2)_2C(=O)O(N$-succinimidyl), —$C(=O)(CH_2)_3C(=O)O(N$-succinimidyl), —$C(=O)(CH_2)_4C(=O)O(N$-succinimidyl), —$C(=O)(CH_2)_5C(=O)O(N$-succinimidyl), —$C(=O)(CH_2)_6C(=O)O(N$-succinimidyl), —$C(=O)(CH_2)_7C(=O)O(N$-succinimidyl), —$C(=O)(CH_2)_8C(=O)O(N$-succinimidyl), or —$C(=O)(CH_2)_9C(=O)O(N$-succinimidyl).

In certain embodiments, the present invention relates to any one of the aforementioned methods, wherein the applicator body further comprises a solid in the fourth internal chamber; and the solid comprises $$XO \overparen{\phantom{XX}O\phantom{XX}}_n OX;$$

wherein n is 80-120 inclusive; and X is —$(CH_2)_3C(=O)O(N$-succinimidyl), —$C(=O)(CH_2)_3C(=O)O(N$-succinimidyl), or —$C(=O)(CH_2)_8C(=O)O(N$-succinimidyl).

In certain embodiments, the present invention relates to any one of the aforementioned methods, wherein the third internal chamber is under partial vacuum.

In certain embodiments, the present invention relates to any one of the aforementioned methods, wherein the fourth internal chamber is under partial vacuum.

In certain embodiments, the present invention relates to any one of the aforementioned methods, further comprising a check valve between the first fluid passageway and the third fluid passageway; and further comprising a check valve between the second fluid passageway and the fourth fluid passageway.

In certain embodiments, the present invention relates to any one of the aforementioned methods, wherein the check valve is a duckbill valve, a caged ball type check valve or an umbrella valve.

In certain embodiments, the present invention relates to any one of the aforementioned methods, wherein the check valve is a duckbill valve.

In certain embodiments, the present invention relates to any one of the aforementioned methods, wherein the nozzle further comprises two precision orifices; the fifth fluid passageway pass through one of said orifices; and the sixth fluid passageway pass through the other of said orifices.

In certain embodiments, the present invention relates to any one of the aforementioned methods, wherein the precision orifices each have a diameter between about 0.002" and about 0.020".

In certain embodiments, the present invention relates to any one of the aforementioned methods, wherein the precision orifices each have a diameter between about 0.004" and about 0.010".

In certain embodiments, the present invention relates to any one of the aforementioned methods, wherein the nozzle further comprises a brush, a sponge, a foam swab, a porous plastic component, a duck bill tip, a textile mitt or a spray tip affixed to the outlet.

In certain embodiments, the present invention relates to any one of the aforementioned methods, wherein the nozzle further comprises a tubular fitment having two open ends; one end of the tubular fitment is affixed to the outlet; and the tubular fitment is adapted to pass through an endoscope or a laparoscope.

In certain embodiments, the present invention relates to any one of the aforementioned methods, wherein the nozzle further comprises a tubular fitment having two open ends; one open end of the tubular fitment is affixed to the outlet and the other open end of the fitment has a flattened opening relative to the open end affixed to the outlet.

In certain embodiments, the present invention relates to any one of the aforementioned methods, wherein the nozzle further comprises a tubular fitment having two open ends; one open end of the tubular fitment is affixed to the outlet and the other open end of the fitment comprises a protruding spatula-like piece.

In certain embodiments, the present invention relates to any one of the aforementioned methods, wherein said applicator is shaped like a pen.

In certain embodiments, the present invention relates to any one of the aforementioned methods, wherein said applicator is shaped like a gun.

In certain embodiments, the present invention relates to any one of the aforementioned methods, wherein said applicator is shaped like a gun; and the applicator further comprises a pistol-style grip.

In certain embodiments, the present invention relates to any one of the aforementioned methods, wherein the applicator further comprises an atomization fluid pathway.

In certain embodiments, the present invention relates to any one of the aforementioned methods, wherein the applicator further comprises an atomization fluid pathway; wherein said atomization fluid pathway is configured to expel any material in the fifth internal chamber out of the nozzle through the outlet.

In certain embodiments, the present invention relates to any one of the aforementioned methods, wherein the applicator further comprises a drive train fluid pathway.

In certain embodiments, the present invention relates to any one of the aforementioned methods, wherein said applicator further comprises a trigger mechanism which controls the movement of one or more plungers or pistons.

In certain embodiments, the present invention relates to any one of the aforementioned methods, wherein said applicator further comprises a trigger mechanism which controls the movement of one or more plungers or pistons; and the trigger comprises a linear two-stage valve.

In certain embodiments, the present invention relates to any one of the aforementioned methods, wherein the applicator further comprises an atomization fluid pathway, a drive train fluid pathway, and a trigger mechanism which controls the movement of one or more barrels, plungers or pistons; wherein the trigger comprises a linear two-stage valve; the first stage of the valve is connected to an atomization fluid pathway; and the second stage of the valve is connected to a drive train fluid pathway.

In certain embodiments, the present invention relates to any one of the aforementioned methods, wherein said applicator further comprises a trigger mechanism which controls the movement of one or more plungers or pistons; and the trigger comprises a linear two-stage valve, and can be mechanically or manually pushed forward to de-energize the applicator.

In certain embodiments, the present invention relates to any one of the aforementioned methods, wherein said applicator further comprises a trigger mechanism which controls the movement of one or more plungers or pistons; and the trigger comprises a button.

In certain embodiments, the present invention relates to any one of the aforementioned methods, wherein the applicator further comprises a power source to cause the first piercer to pierce the first piercable barrier, cause the second piercer to pierce the second piercable barrier, or both.

In certain embodiments, the present invention relates to any one of the aforementioned methods, wherein the applicator further comprises a power source to cause the third piercer to pierce the third piercable barrier, cause the fourth piercer to pierce the fourth piercable barrier, or both.

In certain embodiments, the present invention relates to any one of the aforementioned methods, wherein the applicator further comprises a power source to cause the first piston to move to the second end of the first barrel, to cause the second piston to move to the second end of the second barrel, or both.

In certain embodiments, the present invention relates to any one of the aforementioned methods, wherein the applicator further comprises a power source to cause the third piston to move to the second end of the third barrel, to cause the fourth piston to move to the second end of the fourth barrel, or both.

In certain embodiments, the present invention relates to any one of the aforementioned methods, wherein the applicator further comprises a power source; wherein said power source is contained within the applicator.

In certain embodiments, the present invention relates to any one of the aforementioned methods, wherein the applicator further comprises a power source; wherein said power source is outside of the applicator.

In certain embodiments, the present invention relates to any one of the aforementioned methods, wherein the applicator further comprises a power source; wherein said power source is selected from the group consisting of compressed gas, mechanical power, chemical power, and electrical power.

In certain embodiments, the present invention relates to any one of the aforementioned methods, wherein the applicator further comprises a means to use chemical power as a power source.

In certain embodiments, the present invention relates to any one of the aforementioned methods, wherein the applicator further comprises compressed gas as a power source.

In certain embodiments, the present invention relates to any one of the aforementioned methods, wherein the applicator further comprises a spring as a power source.

In certain embodiments, the present invention relates to any one of the aforementioned methods, wherein the applicator further comprises a means to use manual power as a power source.

In certain embodiments, the present invention relates to any one of the aforementioned methods, wherein the first piercable barrier comprises plastic.

In certain embodiments, the present invention relates to any one of the aforementioned methods, wherein the first piercable barrier comprises metal.

In certain embodiments, the present invention relates to any one of the aforementioned methods, wherein the exterior surface of the first piercable barrier is paper coated with wax or plastic.

In certain embodiments, the present invention relates to any one of the aforementioned methods, wherein the second piercable barrier comprises one or more polymers selected from the group consisting of polyacrylics, silicones, polyolefins, polystyrenes, polyesters, polyethers, polyurethanes, polycarbonates, polyamines, and co-polymers thereof.

In certain embodiments, the present invention relates to any one of the aforementioned methods, wherein the second piercable barrier comprises metal.

In certain embodiments, the present invention relates to any one of the aforementioned methods, wherein the exterior surface of the second piercable barrier is coated with wax or plastic.

In certain embodiments, the present invention relates to any one of the aforementioned methods, wherein the third piercable barrier comprises one or more polymers selected from the group consisting of polyacrylics, silicones, polyolefins, polystyrenes, polyesters, polyethers, polyurethanes, polycarbonates, polyamines, and co-polymers thereof.

In certain embodiments, the present invention relates to any one of the aforementioned methods, wherein the third piercable barrier comprises a metal.

In certain embodiments, the present invention relates to any one of the aforementioned methods, wherein the exterior surface of the third piercable barrier is paper coated with wax or plastic.

In certain embodiments, the present invention relates to any one of the aforementioned methods, wherein the fourth piercable barrier comprises one or more polymers selected from the group consisting of polyacrylics, silicones, polyolefins, polystyrenes, polyesters, polyethers, polyurethanes, polycarbonates, polyamines, and co-polymers thereof.

In certain embodiments, the present invention relates to any one of the aforementioned methods, wherein the fourth piercable barrier comprises a metal.

In certain embodiments, the present invention relates to any one of the aforementioned methods, wherein the exterior surface of the fourth piercable barrier is paper coated with wax or plastic.

In certain embodiments, the present invention relates to any one of the aforementioned methods, wherein the first barrel and the second barrel are mechanically locked such that their ability to advance through the third barrel and the fourth barrel, respectively, is constrained to be substantially simultaneous.

In certain embodiments, the present invention relates to any one of the aforementioned methods, wherein the length of the first barrel is between about 0.5 inches to about 9 inches; or about 1.5 inches to about 4 inches; or about 2 inches to about 3 inches.

In certain embodiments, the present invention relates to any one of the aforementioned methods, wherein the diameter of the first barrel is between about 0.2 inches and about 2 inches; or about 0.3 inches to about 0.75 inches; or about 0.4 inches to about 0.6 inches.

In certain embodiments, the present invention relates to any one of the aforementioned methods, wherein the length of the second barrel is between about 0.5 inches to about 9 inches; or about 1.5 inches to about 4 inches; or about 2 inches to about 3 inches.

In certain embodiments, the present invention relates to any one of the aforementioned methods, wherein the diameter of the second barrel is between about 0.2 inches and about 2 inches; or about 0.3 inches to about 0.75 inches; or about 0.4 inches to about 0.6 inches.

In certain embodiments, the present invention relates to any one of the aforementioned methods, wherein the length of the third barrel is between about 0.5 inches and about 6 inches.

In certain embodiments, the present invention relates to any one of the aforementioned methods, wherein the diameter of the third barrel is between about 0.2 inches and about 2 inches; or about 0.3 inches to about 0.75 inches; or about 0.4 inches to about 0.6 inches.

In certain embodiments, the present invention relates to any one of the aforementioned methods, wherein the length of the fourth barrel is between about 0.5 inches to about 6 inches; or about 1.5 inches to about 4 inches; or about 2 inches to about 3 inches.

In certain embodiments, the present invention relates to any one of the aforementioned methods, wherein the diameter of the fourth barrel is between about 0.2 inches and about 2 inches; or about 0.3 inches to about 0.75 inches; or about 0.4 inches to about 0.6 inches.

In certain embodiments, the present invention relates to any one of the aforementioned methods, wherein the length of the nozzle assembly is between about 0.5 inches and about 15 inches; or about 0.75 inches to about 6 inches; or about 1 inch to about 2 inches.

In certain embodiments, the present invention relates to any one of the aforementioned methods, wherein the diameter of the outlet is between about 0.1 inches and about 1 inch.

One aspect of the invention relates to a method of using an applicator to apply a composition to a surface; wherein the applicator comprises an applicator body and a tubular removable fitment; wherein the tubular removable fitment has a first open end and a second open end; the first open end is attached to the applicator body; and the second open end is adapted to pass through a trocar port in a scope.

In certain embodiments, the present invention relates to any one of the aforementioned methods, wherein the scope is an endoscope or a laparoscope.

One aspect of the invention relates to a method of using an applicator to apply a composition to a surface; wherein the applicator comprises an applicator body and a tubular removable fitment; wherein the tubular removable fitment has a first open end and a second open end; the first open end is attached to the applicator body; and the second open end has a flattened opening relative to the first open end.

One aspect of the invention relates to a method of using an applicator to apply a composition to a surface; wherein the applicator comprises an applicator body and a tubular removable fitment; wherein the tubular removable fitment has a first open end and a second open end; the first open end is attached to the applicator body; and the second open end comprises a protruding spatula-like piece.

In certain embodiments, the present invention relates to any one of the aforementioned methods, wherein the applicator is a spray applicator for tissue adhesives or therapeutic hydrogels.

Sterilization Procedures

A variety of procedures can be used to sterilize the applicators and/or the chemical composition contained therein. Sterilization may be accomplished by, for example, chemical, physical, or irradiation techniques. Examples of chemical methods include exposure to ethylene oxide or hydrogen peroxide vapor. Examples of physical methods include sterilization by heat (dry or moist), retort canning, and filtration. The British Pharmacopoeia recommends heating at a minimum of 160° C. for not less than 2 hours, a minimum of 170° C. for not less than 1 hour and a minimum of 180° C. for not less than 30 minutes for effective sterilization. For examples of heat sterilization, see U.S. Pat. No. 6,136,326, which is hereby incorporated by reference. Passing the chemical composition through a membrane can be used to sterilize a composition. For example, the composition is filtered through a small pore filter such as a 0.22 micron filter which comprises material inert to the composition being filtered. In certain instances, the filtration is conducted in a Class 100,000 or better clean room. Examples of irradiation methods include gamma irradiation, electron beam irradiation, microwave irradiation, and irradiation using visible light. One method is electron beam irradiation, as described in U.S. Pat. Nos. 6,743,858; 6,248,800; and 6,143,805, each of which is hereby incorporated by reference.

There are several sources for electron beam irradiation. The two main groups of electron beam accelerators are: (1) a Dynamitron, which uses an insulated core transformer, and (2) radio frequency (RF) linear accelerators (linacs). The Dynamitron is a particle accelerator (4.5 MeV) designed to impart energy to electrons. The high energy electrons are generated and accelerated by the electrostatic fields of the accelerator electrodes arranged within the length of the glass-insulated beam tube (acceleration tube). These electrons, traveling through an extension of the evacuation beam tube and beam transport (drift pipe) are subjected to a magnet deflection system in order to produce a "canned" beam, prior to leaving the vacuum enclosure through a beam window. The dose can be adjusted with the control of the percent scan, the beam current, and the conveyor speed. In certain instances, the electron-beam radiation employed may be maintained at an initial fluence of at least about 2 $\mu$Curie/cm$^2$, at least about 5 $\mu$Curie/cm$^2$, at least about 8 $\mu$Curie/cm$^2$, or at least about 10 $\mu$Curie/cm$^2$. In certain instances, the electron-beam radiation employed has an initial fluence of from about 2 to about 25 $\mu$Curie/cm$^2$. In certain instances, the electron-beam dosage is from about 5 to 50 kGray, or from about 15 to about 20 kGray with the specific dosage being selected relative to the density of material being subjected to electron-beam radiation as well as the amount of bioburden estimated to be therein. Such factors are well within the skill of the art.

The applicators and/or composition to be sterilized may be in any type of at least partially electron beam permeable container such as glass or plastic. In embodiments of the present invention, the container may be sealed or have an opening. The penetration of electron beam irradiation is a function of the packaging. If there is not enough penetration from the side of a stationary electron beam, the container may be flipped or rotated to achieve adequate penetration. Alternatively, the electron beam source can be moved about a stationary package. In order to determine the dose distribution and dose penetration in product load, a dose map can be performed. This will identify the minimum and maximum dose zone within a product.

Procedures for sterilization using visible light are described in U.S. Pat. No. 6,579,916, which is hereby incorporated by reference. The visible light for sterilization can be generated using any conventional generator of sufficient power and breadth of wavelength to effect sterilization. Generators are commercially available under the tradename PureBright® in-line sterilization systems from PurePulse Technologies, Inc. 4241 Ponderosa Ave, San Diego, Calif. 92123, USA. The PureBright® in-line sterilization system employs visible light to sterilize clear liquids at an intensity approximately 90,000 times greater than surface sunlight. If the amount of UV light penetration is of concern, conventional UV absorbing materials can be used to filter out the UV light.

In one embodiment, the composition in the applicator is sterilized to provide an applicator with a Sterility Assurance Level (SAL) of at least about $10^{-3}$. The Sterility Assurance Level measurement standard is described, for example, in ISO/CD 14937, the entire disclosure of which is incorporated herein by reference. In certain embodiments, the Sterility Assurance Level may be at least about $10^{-4}$, at least about $10^{-5}$, or at least about $10^{-6}$.

As discussed above, in certain embodiments of the present invention, one or more of the compositions, reagents, or components of a kit has been sterilized. The sterilization may be achieved using gamma radiation, e-beam radiation, dry heat sterilization, ethylene oxide sterilization, or a combination of any of them. The compositions, reagents, or components of the kits can be sterilized in an aqueous solution or neat.

In certain embodiments a compound present in an applicator (as described herein) has been sterilized by e-beam radiation between 2-40 kGy; or between 3-20 kGy; or between 5-12 kGy. In certain embodiments, said sterilization is carried out below 30° C. In certain embodiments, said sterilization is carried out below 20° C. In certain embodiments, said sterilization is carried out below 10° C. In certain embodiments, said sterilization is carried out below 0° C.

Kits

In another aspect of the invention kits are provided containing one or more applicators of the invention. A "kit," as used herein, typically defines a package or an assembly including one or more of the applicators of the invention, and/or other compositions associated with the invention, for example, as described herein. Each of the compositions of the kit may be provided in liquid form (e.g., in solution), or in solid form (e.g., a dried powder). In certain cases, some of the compositions may be constitutable or otherwise processable (e.g., to an active form), for example, by the addition of a suitable solvent or other species, which may or may not be provided with the kit. Examples of other compositions or components associated with the invention include, but are not limited to, solvents, surfactants, diluents, salts, buffers, emulsifiers, chelating agents, fillers, antioxidants, binding agents, bulking agents, preservatives, drying agents, antimicrobials, needles, syringes, packaging materials, tubes, bottles, flasks, beakers, dishes, frits, filters, rings, clamps, wraps, patches, containers, and the like, for example, for using, modifying, assembling, storing, packaging, preparing, mixing, diluting, and/or preserving the compositions components for a particular use. In certain embodiments, different parts of the applicators may be packaged separately (e.g., in Mylar pouches).

A kit of the invention may include instructions in any form that are provided in connection with the applicators of the invention in such a manner that one of ordinary skill in the art would recognize that the instructions are to be associated with the compositions of the invention. For instance, the instructions may relate to the use, modification, mixing, diluting, preserving, assembly, storage, packaging, and/or preparation of the applicators and/or other compositions associated with the kit. In some cases, the instructions may also include instructions for the use of the applicators. The instructions may be provided in any form recognizable by a user as a suitable vehicle for containing such instructions; for example, written or published, verbal, audible (e.g., telephonic), digital, optical, visual (e.g., videotape, DVD, etc.) or electronic communications (including Internet or web-based communications), provided in any manner.

Definitions

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The term "nozzle" as used herein is known to those skilled in the art and refers to a mechanical device designed to control the characteristics of a fluid flow as it exits from an enclosed chamber (such as an applicator body) into some medium. A nozzle is often a tube of varying diameter, and it can be used to direct or modify the flow of a liquid or gas. Nozzles are frequently used to control the rate of flow, speed, direction, and/or the pressure of the stream that emerges from them. In certain embodiments the proximal end of a nozzle, wherein the fluid flow enters, will have a larger diameter than the distal end of a nozzle, where the fluid flow exists. This is known as a convergent nozzle (i.e., narrowing down from a wide diameter to a smaller diameter in the direction of the flow). In other embodiments the nozzle can be characterized as divergent (i.e., expanding from a smaller diameter to a larger one).

A trocar is a hollow cylinder with a sharply pointed end, often three-sided, that is used to introduce cannulas and other similar implements into blood vessels or body cavities. Trocars are also used as ports in laparoscopic surgery. A trocar is often passed inside a cannula, and functions as a portal for the subsequent placement of other devices, such as a chest drain or intravenous cannula. In certain embodiments described herein, the nozzle of the apparatus is designed to pass through a trocar port or equivalent on a endoscope or laproscope.

The term "brush" or "brush cannula" as used herein is known to those skilled in the art. The name represents the function of the brush: It is constructed to enable liquid to flow through the bristles for an application. The brushes can be attached to a wide variety of media that dispense liquid, and can be made out of many types of bristle material and configurations. In certain embodiments herein the brush cannula is connected to an applicator body. Brush cannulas are also known as flow-thru brushes; the terms are used interchangeably herein.

The term "activated PEG" as used herein is known to those skilled in the art and refers to poly(ethylene) glycols which typically have either both ends activated for conjugation with other molecules, or have one end capped as an ether (e.g., a methyl ether) and the other end activated for conjugation with another molecule. Shown below are chemical structures for polyethylene glycol (PEG), mono-methylated polyethylene glycol (mPEG), and an activated mPEG.

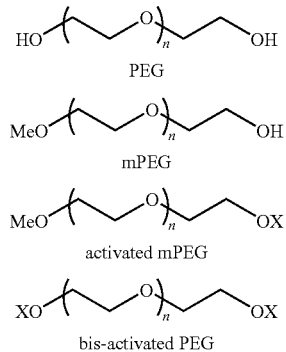

In the structures provided above n is a positive integer. In a batch of activated PEG different individual molecules will have a different values of n (i.e., the mixture is polydisperse); these mixtures are often characterized by an average molecular weight, which can be converted into an average value for n. In certain embodiments herein, the average n is between about 10 and about 200. In other embodiments the average n is between about 80 and about 120. In yet other embodiments, the average n is about 100. In the structures provided above, X can comprise a variety of chemical moieties, such as, for example, a N-succinimide, a N-maleimide, a nitro, an aldehyde, an amine, a thiol, a ketal, an acetal, or a carbonate. In certain embodiments, X is selected from the group consisting of —$CH_2C(=O)O$(N-succinimidyl), —$(CH_2)_2C(=O)O$(N-succinimidyl), —$(CH_2)_3C(=O)O$(N-succinimidyl) ["PEG-SPA"], —$(CH_2)_4C(=O)O$(N-succinimidyl), —$(CH_2)_5C(=O)O$(N-succinimidyl), —$(CH_2)_6C(=O)O$(N-succinimidyl), —$(CH_2)_7C(=O)O$(N-succinimidyl), —$(CH_2)_8C(=O)O$(N-succinimidyl), —$(CH_2)_9C(=O)O$(N-succinimidyl), —$C(=O)CH_2C(=O)O$(N-succinimidyl), —$C(=O)(CH_2)_2C(=O)O$(N-succinimidyl), —$C(=O)(CH_2)_3C(=O)O$(N-succinimidyl) ["PEG-SG"], —$C(=O)(CH_2)_4C(=O)O$(N-succinimidyl) ["PEG-adipate"], —$C(=O)(CH_2)_5C(=O)O$(N-succinimidyl), —$C(=O)(CH_2)_6C(=O)O$(N-succinimidyl), —$C(=O)(CH_2)_7C(=O)O$(N-succinimidyl), —$C(=O)(CH_2)_8C(=O)O$(N-succinimidyl) ["PEG-sebacate"], —$C(=O)(CH_2)_9C(=O)O$(N-succinimidyl), —$C(=O)$(p-nitrophenyl), —$CH_2CH_2C(=O)H$, —$CH_2CH_2CH_2NH_2$, —$CH_2CH_2CH(OCH_2CH_3)_2$, —$CH_2CH_2SH$, —$CH_2CH_2CH_2N(H)C(=O)CH_2CH_2$(N-maleimidyl), and —$O(C=O)O$(p-nitrophenyl).

The term "PEG(NHS)$_2$" refers to a polyethylene glycol having —$C(=O)O$((N-succinimidyl) at both ends of the polymer chain. PEG(NHS)$_2$ can be prepared in variety of ways, such as by using either of the following methods. In method 1, a polyethylene glycol is subjected to oxidative conditions in order to oxidize the two termini to the corresponding carboxylic acids [$HO_2CCH_2O$-PEG-$OCH_2CO_2H$], followed by transformation to the bis(NHS ester). In method 2, PEG(NHS)$_2$ is prepared by alkylation of the two termini of a polyethylene glycol with acrylonitrile to give $NCCH_2CH_2O$-PEG-$OCH_2CH_2CN$, followed by hydrolysis to the bis(acid) [$HO_2CCH_2CH_2O$-PEG-$OCH_2CH_2CO_2H$], and then transformation to the bis(NHS ester).

As used here, "PEG-SPA" refers to the following structure:

$$XO-(CH_2-CH_2-O)_n-CH_2-CH_2-OX$$

wherein X is —$(CH_2)_3C(=O)O$(N-succinimidyl); and n is an integer (e.g., from 10 to 200).

As used herein, "PEG-SG" refers to the following structure:

$$XO-(CH_2-CH_2-O)_n-CH_2-CH_2-OX$$

wherein X is —$C(=O)(CH_2)_3C(=O)O$(N-succinimidyl); and n is an integer (e.g., from 10 to 200).

As used herein, "PEG-adipate" refers to the following structure:

$$XO-(CH_2-CH_2-O)_n-CH_2-CH_2-OX$$

wherein X is —$C(=O)(CH_2)_4C(=O)O$(N-succinimidyl); and n is an integer (e.g., from 10 to 200).

As used herein, "PEG-sebacate" refers to the following structure:

$$XO-(CH_2-CH_2-O)_n-CH_2-CH_2-OX$$

wherein X is —$C(=O)(CH_2)_8C(=O)O$(N-succinimidyl); and n is an integer (e.g., from 10 to 200).

As used herein, "plastic" refers to polyacrylics, silicones, polyolefins, polystyrenes, polyesters, polyethers, polyurethanes, polycarbonates, polyamines, and co-polymers thereof.

As used herein, "silicones" (polymerized siloxanes or polysiloxanes) are mixed inorganic-organic polymers with the chemical formula $[R_2SiO]_n$, where R may be an organic group such as methyl, ethyl, and phenyl. These materials consist of an inorganic silicon-oxygen backbone with organic side groups attached to the silicon atoms, which are four-coordinate. In some cases organic side groups can be used to link two or more of these backbones together. By varying the —Si—O— chain lengths, side groups, and crosslinking, silicones can be synthesized with a wide variety of properties and compositions.

As used herein, the term "patient" refers to any animal in need, including primates, in particular humans, and other mammals such as equines, cattle, swine and sheep; and poultry and pets in general.

As used herein, "partial vacuum" refers to a pressure which is less than atmospheric pressure (approx. 100 kPa) but greater than 1 kPa.

The term "check valve" as used herein refers to a mechanical device, a valve, which normally allows fluid to flow through it in only one direction.

The term "solid" as used herein includes viscous liquids such as polyalkyleneimines.

EXEMPLIFICATION

The invention now being generally described, it will be more readily understood by reference to the following examples which are included merely for purposes of illustration of certain aspects and embodiments of the present invention, and are not intended to limit the invention.

Example 1

In certain embodiments, the device is configured to be an applicator for a reactive hydrogel system. The formulation consists of two formulation parts which do not mix until the final stage whereupon the mixed formulation exits the applicator. The first formulation part consists of two separate constituents; a buffer solution and an activated poly ethylene glycol (PEG) powder. The second formulation part consists of a buffer solution and a separate crosslinking agent of poly ethyleneimine (PEI). The applicator system thus consists of two sets of two receptacles. In the proximal end of the device, the buffer solution of formulation part A and the buffer solution of part B are housed. In the more distal end of the device, the PEG powder of part A and the PEI of part B are housed. A pictorial of this arrangement can be seen in FIG. 1.

Figure 2:
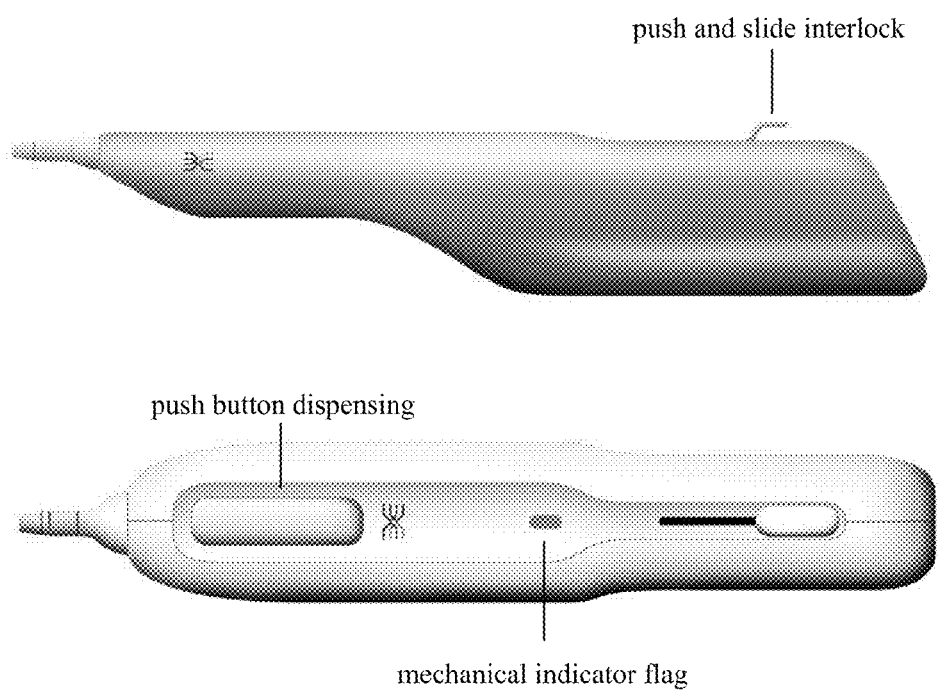
Figure 3:
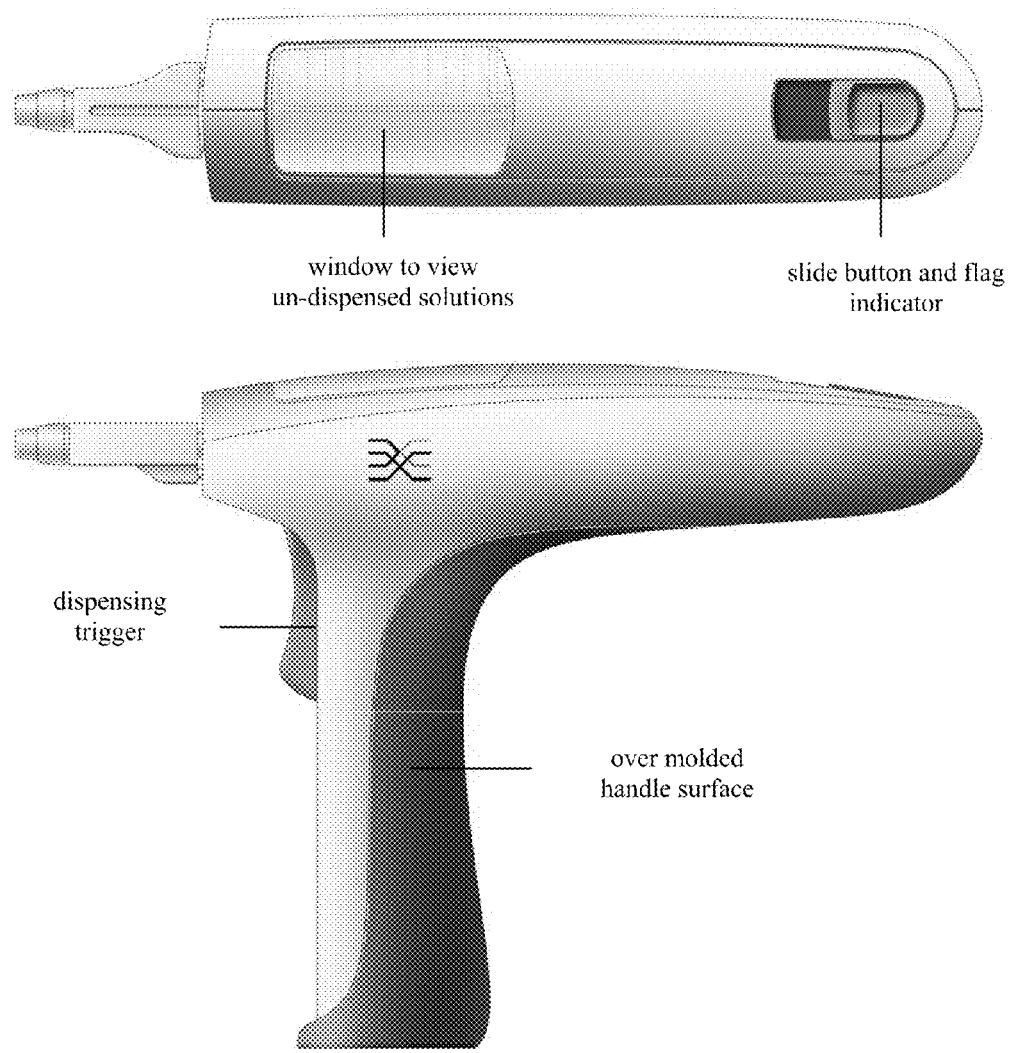

As stated previously, there are several form factors that can be utilized to house the invention. In FIGS. 2 and 3 are shown a pen style form factor as well as a gun style form factor.

Figure 4:
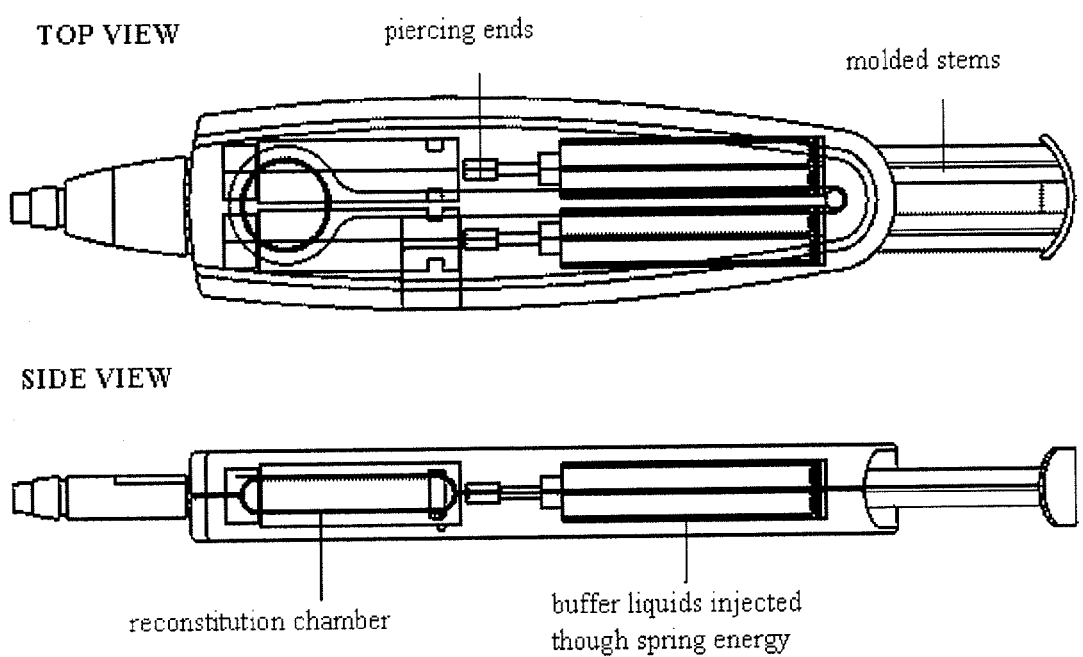
Figure 5:
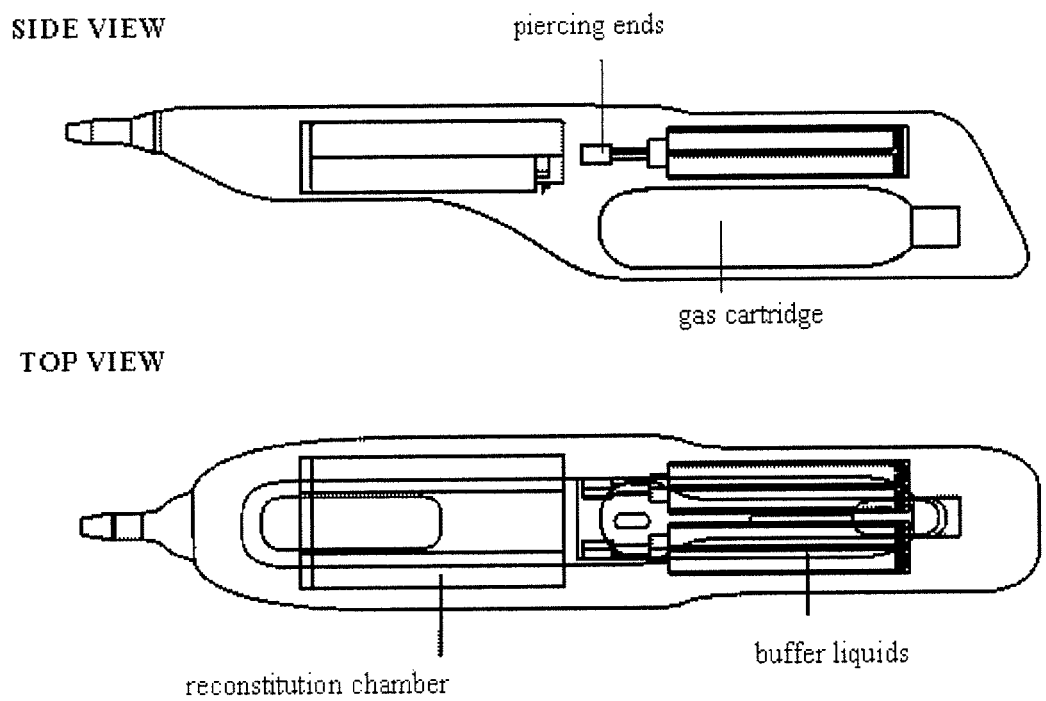
Figure 6:
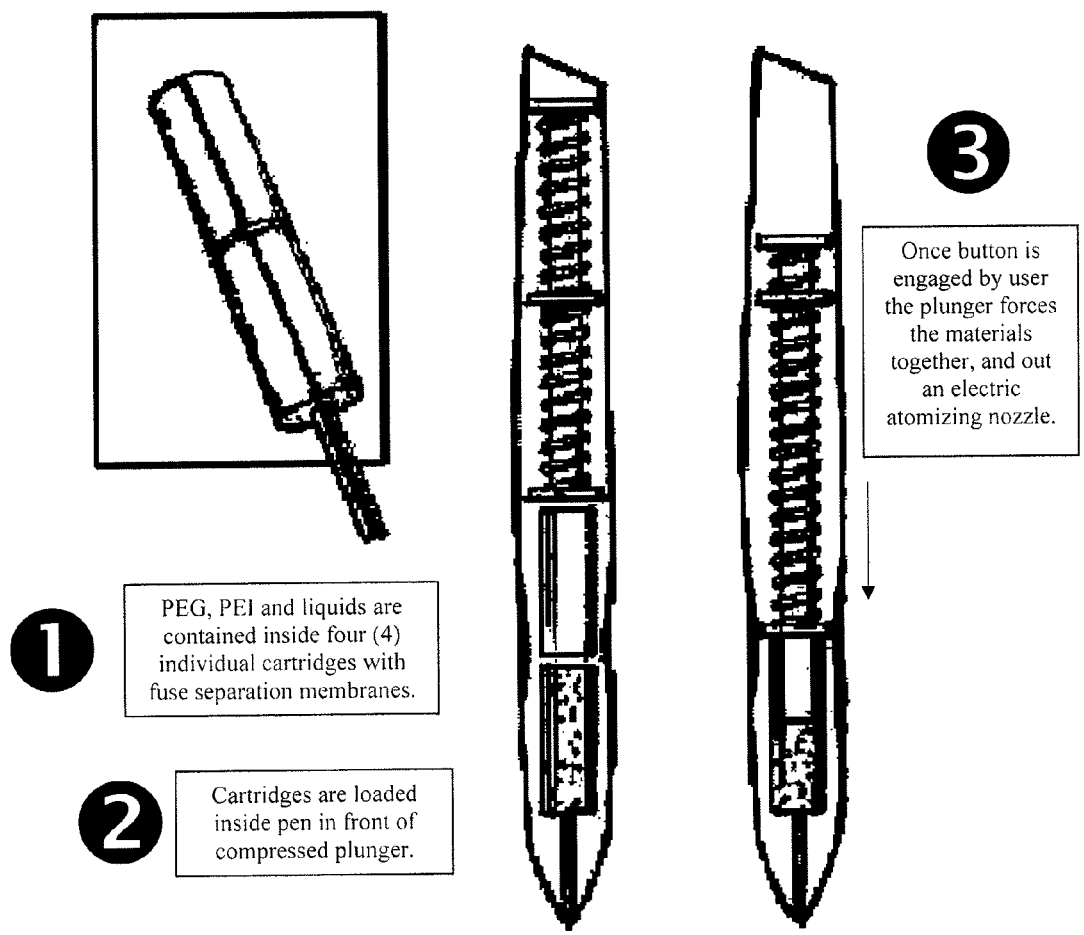

As stated previously, the device can be powered using any one of several energy choices. In FIGS. 4-6 are pen form factor devices with mechanical spring energy, compressed gas, or electricity as power sources. Similar gun form factor devices could easily be devised by one skilled in the art.

Figure 7:
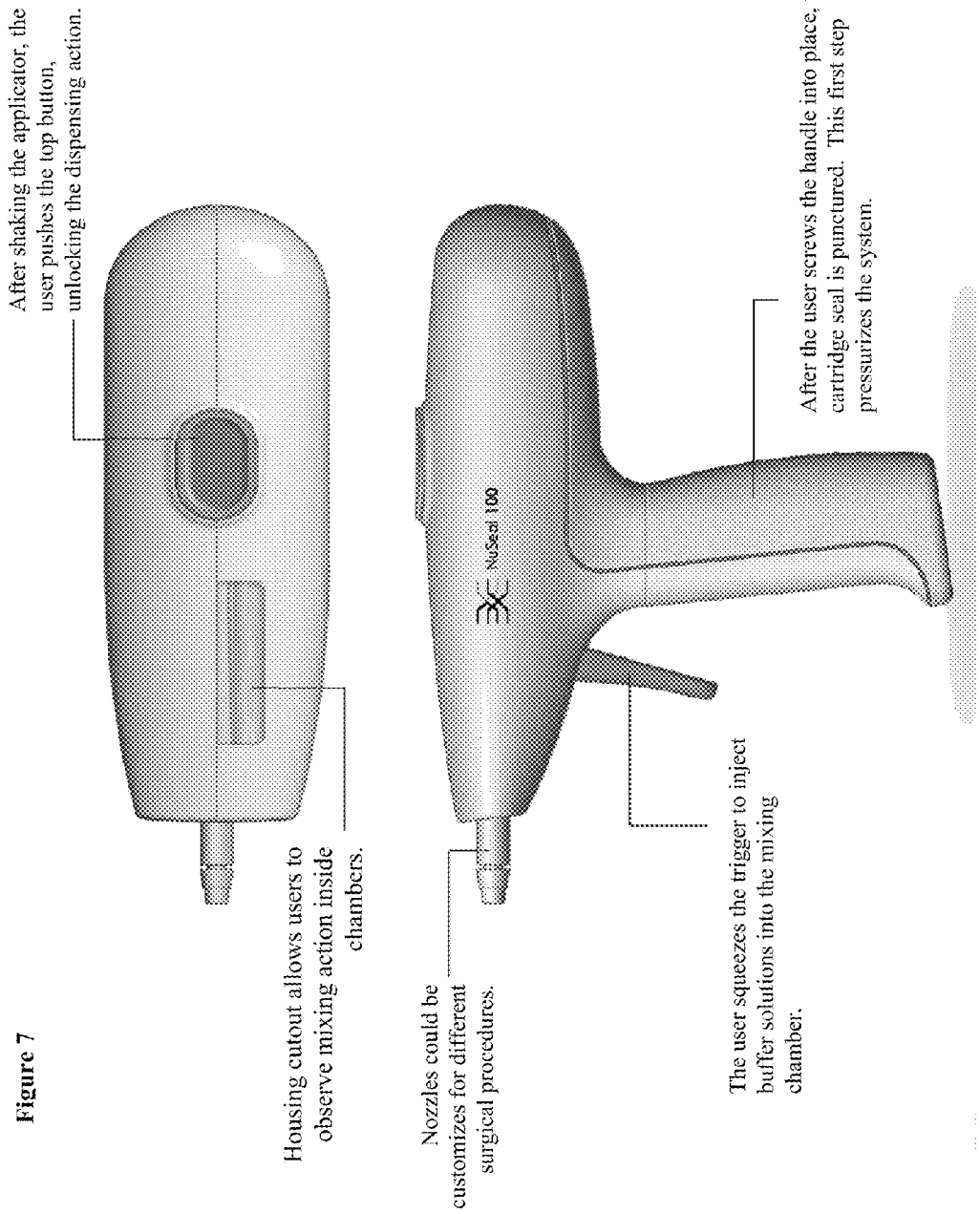
Figure 8:
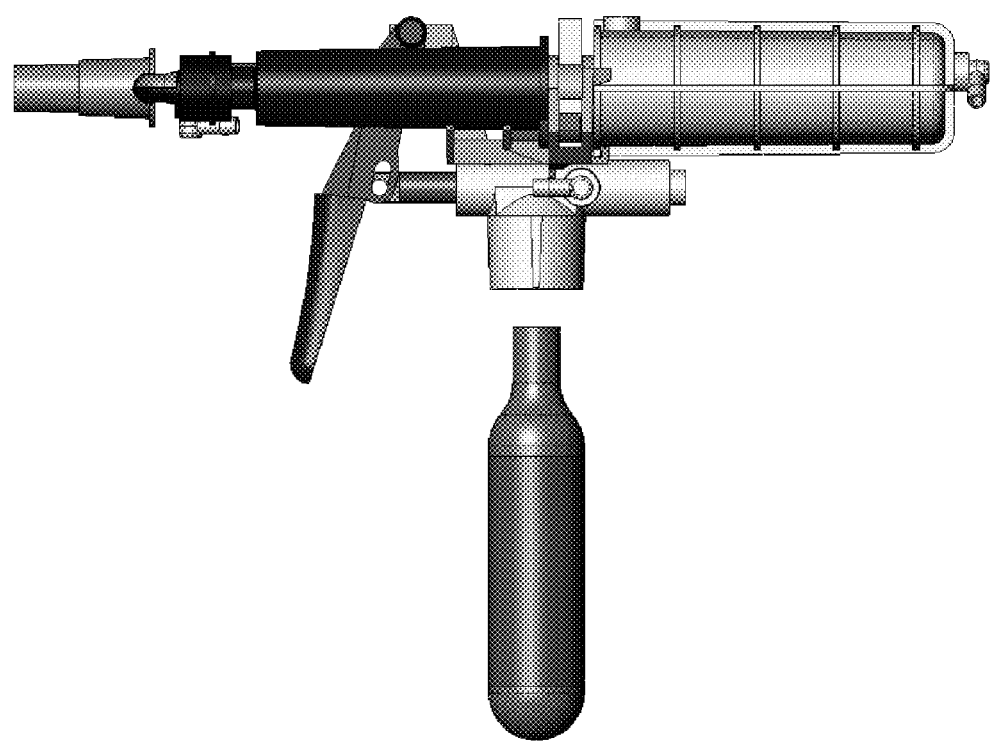

In one embodiment, the device is configured as a gun form factor applicator for an atomized spray of a reactive hydrogel formulation. The hydrogel consists of two parts, each part further consisting of two components. Part A of the formulation has in the most proximal receptacle a buffer solution and in the distal end, a receptacle for activated PEG powder. Part B of the formulation has in the most proximal receptacle a buffer solution and in the more distal receptacle PEI. The energy source is compressed gas which also acts as a means of instantly atomizing the reconstituted formulation and conveying it to the surface to be treated. A pictures of the device are shown in FIGS. 7 and 8.

This embodiment has several unique design features. First, the trigger mechanism is a linear two-stage valve. Once the compressed gas cylinder is engaged, the trigger assembly and valve are in the off position. In this position, the valve contains the gas within the cylinder only and the rest of the gun is not pressurized. As the trigger is depressed, linear actuation of the value engages the atomization pathway. Further depression of the trigger further moves the linear actuator of the valve assembly and it engages the drive train pathway. Upon release, a spring (or springs) pushes the linear actuator of the valve assembly forward away from the valve body and thus first disengages from the drive train pathway and then disengages from the atomization pathway. This is an important feature of the system as it allows for reactive chemistry systems to be mixed, atomized and delivered through the nozzle and upon release of the trigger, the drive train stops pushing reconstituted formulation forward and the compressed gas which is still engaged clears the nozzle of mixed formulation before it has a chance to solidify thus clogging the nozzle. Without this feature, the device could not be reused without partial disassembly and the addition of new unused nozzle parts.

In an embodiment of the above trigger mechanism, the trigger is further designed such that in addition to the two-stage valve mechanism described above, the trigger can also be pushed forward toward the nozzle end of the gun applicator. This moves the linear actuator forward, away from the valve body and allows the device to vent all pressurized gas from the cylinder to the ambient environment, rendering the gun completely de-energized and ready for incineration or other disposal.

In certain embodiments, the mixing chamber/nozzle assembly incorporates two fluid pathways which convey the two reconstituted formulation parts into the chamber by means of energizing the drive train pathway. An additional two compressed gas streams are conveyed into the mixing chamber/nozzle assembly when the atomization pathway is energized. The design is made to completely mix the two formulation parts and atomize the mixed formulation and expel it through the nozzle and onto the surface to be treated.

Another aspect of certain embodiments is that the final expulsion of reconstituted formulation occurs with a twin syringe-like mechanism which is mechanically locked between part A and part B of the formulation. This guarantees that the final mix of formulation parts is in the correct stoichiometric ratio. This is very important for most reactive chemistry systems because the ratio of part A to part B (or more parts) is important to the quality of the mixed formulation or the reaction rate of the mixed formulation. The ratios of the different parts may be controlled by controlling the relative size of the diameter of the syringe-like receptacles.

Yet another aspect of certain embodiments is that the front chambers can be stored under partial vacuum. This partial vacuum is necessary to allow the buffer reservoirs to expel their contents into the front PEI and PEG chambers without causing an additional build up of pressure or premature leakage of the reconstituted formulation parts. This partial vacuum can be applied directly during the filling of the front reservoirs or may be applied manually after filling by filling the reservoirs, then advancing the plunger, sealing the front end of the reservoir and finally extracting the plunger backward and locking it in place.

A further design feature of certain embodiments is that there is a mechanical interlock or gate which prevents final mixing of parts A and B of the formulation. This allows the user to perform a first depression of the trigger which energizes both the atomization pathway and the drive train pathway. The buffer solution receptacles then move forward and engage the PEI and PEG receptacles and expel the buffers into their respective PEI or PEG receptacles. Further advancement of the drive train is stopped by the lockout thus preventing the gun applicator from mixing the two parts of the formulation. Only after the device is fully reconstituted and the physician is ready to spray a mixed formulation is the lockout or gate button pushed which then allows, upon the next trigger pull a spray of mixed formulation to be applied to the surface to be treated.

Example 2

A method of operation for certain embodiments of the invention, such as those shown in FIGS. 1, 2, 4, 5 and 6, is as follows:

First the user engages the gas bottle or pulls back on a spring to energize it.

Then, the user pulls the trigger which pressurizes the rear housing or engages a spring. By so doing, pressure or force from the spring moves the "buffer syringe" forward, thereby engaging the middle plunger portion of the front mixing chamber (i.e., the reconstitution syringe).

The "buffer flow cap" then moves up stream, opening the fluid port.

The "buffer plunger" forces fluid into reconstitution syringe.

The user hand mixes (e.g., by shaking the device) to reconstitute solid PEG and PEI which was it the reconstitution syringe.

Once the solids are reconstituted, the user removes the "separation tabs".

With the separation tabs removed, the reconstitution assembly moves forward onto the "piercing standoff", thereby breaking the foil seal of reconstitution fluid cap.

The reconstitution plunger then dispenses fluid through nozzle.

Air flows from pressure chamber into nozzle to aid mixing and dispensing.

Example 3

A method of operation for certain embodiments of the invention, such as those shown in FIGS. 3, 7 and 8, is as follows:

First, the device is removed form its packaging and readied for reconstitution.

Then, a user twists the handle to pierce the compressed gas canister and prime the device.

Pulling the trigger engages the atomization pathway first and then the drive train pathway. The drive train pathway pressurizes the rear pressure vessel which pushes the buffer carriers forward. They engage the back end of the PEI and PEG receptacles and are stopped from additional forward motion by the gate or lockout mechanism. The internal floating plungers within the rear buffer carriers then advance and expel the buffers into the PEI and PEG containing receptacles.

The trigger is released which disengages the drive train fluid pathway and then disengages the atomization fluid pathway.

The user then shakes the device in order to ensure thorough reconstitution of the PEI and PEG.

The lockout/gate mechanism is then pushed to free the advance of the rear buffer receptacles.

The trigger is pulled a second time which first engages the atomization pathway and then engages the drive train pathway. Once the drive train pathway is engaged, the rear buffer receptacles advance forcing parts A (PEG solution) and B (PEI Solution) into the atomization/nozzle assembly. In the atomization/nozzle assembly the two parts of the formulation are mixed and atomized and instantly expelled through the nozzle onto the surface to be treated.

The trigger is then released which first disengages the drive train pathway. With the atomization pathway still engaged for a second or two, the atomization gas clears any remaining mixed formulation before disengagement of the atomization pathway occurs.

A second trigger pull reengages the atomization pathway first then engages the drive train pathway. The gun then delivers atomized mixed formulation as before. Release of the trigger acts as described above to stop the delivery of mixed formulation and clears the nozzle with compressed gas before finally stopping all gas delivery.

The device can thus be used for several applications of mixed formulation.

INCORPORATION BY REFERENCE

All of the U.S. patents and U.S. published patent applications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. An applicator, comprising a rear housing, a front housing, a mechanical interlock and a nozzle assembly; wherein
(i) the rear housing comprises:
a first barrel, having a first diameter; a first end; a second end; a first internal chamber; a first piercer, attached to the second end of the first barrel, having a first fluid passageway; and a first plunger, having a first end and a second end, located at least partially within the first internal chamber and under pressure moveable therethrough; and
a second barrel having a second diameter; a first end; a second end; a second internal chamber; a second piercer, located on the second end of the second barrel, having a second fluid passageway; and a second plunger, having a first end and a second end, located at least partially within the second internal chamber and under pressure moveable therethrough;
(ii) the front housing comprises:
a third barrel, having a third diameter; a first end; a second end; a third internal chamber; a first piston having a third fluid passageway therethrough, located within the third internal chamber and under pressure moveable therethrough; a first piercable barrier, located at the first end of the third barrel and suitably positioned to be pierced by the first piercer, thereby allowing fluid communication between the first internal chamber and the second internal chamber via the first fluid passageway and the third fluid passageway; and a second piercable barrier, located at the second end of the third barrel; and
a fourth barrel, having a fourth diameter; a first end; a second end; a fourth internal chamber; a second piston having a fourth fluid passageway therethrough, located within the fourth internal chamber and under pressure moveable therethrough; a third piercable barrier, located at the first end of the fourth barrel and suitably positioned to be pierced by the second piercer, thereby allowing fluid communication between the second internal chamber and the fourth internal chamber via the second fluid passageway and the fourth fluid passageway; and a fourth piercable barrier, located at the second end of the fourth barrel; and
(iii) the nozzle assembly comprises:
a fifth internal chamber; having a first inlet with a third piercer affixed thereto, which comprises a fifth fluid passageway, and is suitably positioned at the first inlet to pierce the second piercable barrier and thereby allow fluid communication between the third internal chamber and the fifth internal chamber via the fifth fluid passageway; a second inlet with a fourth piercer affixed thereto, which comprises a sixth fluid passageway, and is suitably positioned at the second inlet to pierce the fourth piercable barrier and thereby allow fluid communication between the fourth internal chamber and the fifth internal chamber via the sixth fluid passageway; and an outlet;
wherein the nozzle assembly is connected to the front housing; the front housing is connected to the rear housing; the first diameter is less than the third diameter; the second diameter is less than the fourth diameter; the first piercer is sized to block the first fluid passageway; the second piercer is sized to block the second fluid passageway; and the mechanical interlock is positioned to allow initially the first piercer to pierce the first barrier but not block the first fluid passageway; and the mechanical interlock is positioned to initially allow the second piercer to pierce the second barrier but not block the second fluid passageway.

2. The applicator of claim 1, wherein the applicator body further comprises a liquid in the first internal chamber.

3. The applicator of claim 1, wherein the applicator body further comprises a liquid in second internal chamber.

4. The applicator of claim 1, wherein the applicator body further comprises a solid in the third internal chamber.

5. The applicator of claim 4, wherein the solid comprises a polyalkyleneimine.

6. The applicator of claim 1, wherein the applicator body further comprises a viscous liquid in the third internal chamber; and the viscous liquid comprises PEI.

7. The applicator of claim 1, wherein the applicator body further comprises a solid in the fourth internal chamber; and the solid comprises a PEG(NHS)$_2$ or a mixture of two or more PEG(NHS)$_2$.

8. The applicator of claim 1, wherein the applicator body further comprises a solid in the fourth internal chamber; and the solid comprises

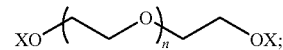

wherein n is 10-200 inclusive; and X is —CH$_2$C(=O)O(N-succinimidyl), —(CH$_2$)$_2$C(=O)O(N-succinimidyl), —(CH$_2$)$_3$C(=O)O(N-succinimidyl), —(CH$_2$)$_4$C(=O)O(N-succinimidyl), —(CH$_2$)$_5$C(=O)O(N-succinimidyl), —(CH$_2$)$_6$C(=O)O(N-succinimidyl), —(CH$_2$)$_7$C(=O)O(N-succinimidyl), —(CH$_2$)$_8$C(=O)O(N-succinimidyl), —(CH$_2$)$_9$C(=O)O(N-succinimidyl), —C(=O)CH$_2$C(=O)O(N-succinimidyl), —C(=O)(CH$_2$)$_2$C(=O)O(N-succinimidyl), —C(=O)(CH$_2$)$_3$C(=O)O(N-succinimidyl), —C(=O)(CH$_2$)$_4$C(=O)O(N-succinimidyl), —C(=O)(CH$_2$)$_5$C(=O)O(N-succinimidyl), —C(=O)(CH$_2$)$_6$C(=O)O(N-succinimidyl), —C(=O)(CH$_2$)$_7$C(=O)O(N-succinimidyl), —C(=O)(CH$_2$)$_8$C(=O)O(N-succinimidyl), or —C(=O)(CH$_2$)$_9$C(=O)O(N-succinimidyl).

9. The applicator of claim 1, further comprising a check valve between the first fluid passageway and the third fluid passageway; and further comprising a check valve between the second fluid passageway and the fourth fluid passageway.

10. The applicator of claim 1, wherein the nozzle further comprises two precision orifices; the fifth fluid passageway pass through one of said orifices; and the sixth fluid passageway pass through the other of said orifices.

11. The applicator of claim 1, wherein the nozzle further comprises a brush, a sponge, a foam swab, a porous plastic component, a duck bill tip, a textile mitt or a spray tip affixed to the outlet.

12. The applicator of claim 1, wherein the nozzle further comprises a tubular fitment having two open ends; one open end of the tubular fitment is affixed to the outlet and the other open end of the fitment comprises a protruding spatula-like piece.

13. The applicator of claim 1, further comprising an atomization fluid pathway; wherein said atomization fluid pathway is configured to expel any material in the fifth internal chamber out of the nozzle through the outlet.

14. The applicator of claim 1, wherein said applicator further comprises a trigger mechanism which controls the movement of one or more plungers or pistons.

15. The applicator of claim 1, further comprising a power source; wherein said power source is contained within the applicator.

16. The applicator of claim 15, wherein said power source is selected from the group consisting of compressed gas, mechanical power, chemical power, and electrical power.

17. The applicator of claim 1, wherein the first barrel and the second barrel are mechanically locked such that their ability to advance through the third barrel and the fourth barrel, respectively, is constrained to be substantially simultaneous.

18. The applicator of claim 1, wherein the applicator body further comprises a buffer in the first internal chamber; a buffer in the second internal chamber; PEI in the third internal chamber; and PEG(NHS)$_2$ in the fourth internal chamber.

19. A method of using an applicator to apply a composition to a surface;
wherein the applicator comprises a rear housing, a front housing, a mechanical interlock and a nozzle assembly; wherein
(i) the rear housing comprises:
a first barrel, having a first diameter; a first end; a second end; a first internal chamber containing a first liquid; a first piercer, attached to the second end of the first barrel, having a first fluid passageway; and a first plunger, having a first end and a second end, located at least partially within the first internal chamber and under pressure moveable therethrough; and
a second barrel having a second diameter; a first end; a second end; a second internal chamber containing a second liquid; a second piercer, located on the second end of the second barrel, having a second fluid passageway; and a second plunger, having a first end and a second end, located at least partially within the second internal chamber and under pressure moveable therethrough;
(ii) the front housing comprises:
a third barrel, having a third diameter; a first end; a second end; a third internal chamber containing a first solid; a first piston having a third fluid passageway therethrough, located within the third internal chamber and under pressure moveable therethrough; a first piercable barrier, located at the first end of the third barrel and suitably positioned to be pierced by the first piercer, thereby allowing fluid communication between the first internal chamber and the second internal chamber via the first fluid passageway and the third fluid passageway; and a second piercable barrier, located at the second end of the third barrel; and
a fourth barrel, having a fourth diameter; a first end; a second end; a fourth internal chamber containing a second solid; a second piston having a fourth fluid passageway therethrough, located within the fourth internal chamber and under pressure moveable therethrough; a third piercable barrier, located at the first end of the fourth barrel and suitably positioned to be pierced by the second piercer, thereby allowing fluid communication between the second internal chamber and the fourth internal chamber via the second fluid passageway and the fourth fluid passageway; and a fourth piercable barrier, located at the second end of the fourth barrel; and (iii) the nozzle assembly comprises:
a fifth internal chamber; having a first inlet with a third piercer affixed thereto, which comprises a fifth fluid passageway, and is suitably positioned at the first inlet to pierce the second piercable barrier and thereby allow fluid communication between the third internal chamber and the fifth internal chamber via the fifth fluid passageway; a second inlet with a fourth piercer affixed thereto, which comprises a sixth fluid passageway, and is suitably positioned at the second inlet to pierce the fourth piercable barrier and thereby allow fluid communication between the fourth internal chamber and the fifth internal chamber via the sixth fluid passageway; and an outlet;
wherein the nozzle assembly is connected to the front housing; the front housing is connected to the rear housing; the first diameter is less than the third diameter; the second diameter is less than the fourth diameter; the first piercer is sized to block the first fluid passageway; the second piercer is sized to block the second fluid passageway; and the mechanical interlock is positioned to allow initially the first piercer to pierce the first barrier but not block the first fluid passageway; and the mechanical interlock is positioned to initially allow the second piercer to pierce the second barrier but not block the second fluid passageway;
comprising the steps of:
advancing the first barrel towards the nozzle and into the third barrel, thereby piercing the first barrier, placing the first internal chamber in fluid communication with the third internal chamber;
advancing the first plunger towards the nozzle, thereby expelling the first liquid into the third internal chamber, forming a first mixture of the first liquid and the first solid;
advancing the second barrel towards the nozzle and into the fourth barrel, thereby piercing the second barrier, placing the second internal chamber in fluid communication with the fourth internal chamber;
advancing the second plunger towards the nozzle, thereby expelling the second liquid into the fourth internal chamber, forming a second mixture of the first liquid and the first solid;
advancing the third barrel towards the nozzle, thereby piercing the third barrier and placing the third internal chamber in fluid communication with the fifth internal chamber;
advancing the fourth barrel towards the nozzle, thereby piercing the fourth barrier, placing the fourth internal chamber in fluid communication with the fifth internal chamber;
advancing the first piston and the second piston towards the nozzle, thereby causing the first mixture to mix with the second mixture in the fifth internal chamber, forming a pre-composition mixture;
applying the pre-composition mixture to the surface, wherein the mixture gels to form the composition on the surface.

20. The method of claim 19, wherein the surface is dura matter, abdominal tissue, tissue adjacent to a spine, internal tissue, lung tissue, intestinal tissue, a cornea, or any internal surface.

* * * * *